x> US009546739B2

United States Patent
Shreve et al.

(10) Patent No.: US 9,546,739 B2
(45) Date of Patent: Jan. 17, 2017

(54) MODULAR SOLENOID VALVE KITS AND ASSOCIATED METHODS

(71) Applicant: Waters Technologies Corporation, Milford, MA (US)

(72) Inventors: Joshua A. Shreve, Franklin, MA (US); Steven D. Trudeau, Webster, MA (US); Paul Keenan, Harrisville, RI (US)

(73) Assignee: Waters Technologies Corporation, Milford, MA (US)

( * ) Notice: Subject to any disclaimer, the term of this patent is extended or adjusted under 35 U.S.C. 154(b) by 109 days.

(21) Appl. No.: 14/381,973

(22) PCT Filed: Mar. 7, 2013

(86) PCT No.: PCT/US2013/029561
§ 371 (c)(1),
(2) Date: Aug. 28, 2014

(87) PCT Pub. No.: WO2013/134485
PCT Pub. Date: Sep. 12, 2013

(65) Prior Publication Data
US 2015/0059865 A1    Mar. 5, 2015

Related U.S. Application Data

(60) Provisional application No. 61/607,952, filed on Mar. 7, 2012.

(51) Int. Cl.
*F16K 27/02*  (2006.01)
*F16K 31/06*  (2006.01)
(Continued)

(52) U.S. Cl.
CPC ............. *F16K 27/0281* (2013.01); *F16K 1/34* (2013.01); *F16K 1/38* (2013.01); *F16K 27/029* (2013.01);
(Continued)

(58) Field of Classification Search
CPC ...... F16K 27/0281; F16K 27/029; F16K 1/34; F16K 1/38; F16K 31/0655
(Continued)

(56) References Cited

U.S. PATENT DOCUMENTS 2,988,080 A    6/1961  Rankl
3,143,131 A *  8/1964  Spencer ................. F16K 31/10
                                                          137/269

(Continued)

OTHER PUBLICATIONS

Guiochon G, et al., Fundamental challenges and opportunities for preparative supercritical fluid chromatography. J Chromatogr A. Feb. 25, 2011;1218(8):1037-114.
(Continued)

*Primary Examiner* — Kevin Lee
(74) *Attorney, Agent, or Firm* — McCarter & English, LLP; Deborah M. Vernon; Patrick A. Walker, III

(57) ABSTRACT

Exemplary embodiments are directed to modular solenoid valve kits and associated methods, generally involving a valve body that includes a plurality of actuator section components and a plurality of head section components. The plurality of actuator section components includes a drive solenoid, a solenoid return spring, a stroke calibration collar and an actuator-to-head calibration collar. The plurality of head section components includes a needle, a stem return spring, a seal and a seat. The plurality of actuator section components and head section components are adapted to be interchanged to create a pull-through normally open valve, a pull-through normally closed valve, a push-in normally open valve and a push-in normally closed valve. That is, the kits and methods allow for modification of one valve type (e.g., a pull-through normally open valve, a pull-through normally closed valve, a push-in normally open valve and a push-in normally closed valve) into a different type.

38 Claims, 33 Drawing Sheets

(51) Int. Cl.
*G01N 30/36* (2006.01)
*F16K 1/34* (2006.01)
*F16K 1/38* (2006.01)
*G01N 30/32* (2006.01)

(52) U.S. Cl.
CPC ........... *F16K 31/0655* (2013.01); *G01N 30/36* (2013.01); *G01N 2030/328* (2013.01); *Y10T 137/0491* (2015.04); *Y10T 137/5283* (2015.04)

(58) Field of Classification Search
USPC ....................................... 137/269–271, 15.18
See application file for complete search history.

(56) References Cited

U.S. PATENT DOCUMENTS

| | | | | |
|---|---|---|---|---|
| 3,878,859 | A * | 4/1975 | Grob | F16K 31/0668 137/270 |
| 4,978,074 | A | 12/1990 | Weinand | |
| 4,986,299 | A * | 1/1991 | Schultz | B60C 23/001 137/269 |
| 5,246,205 | A | 9/1993 | Gillingham et al. | |
| 5,669,406 | A * | 9/1997 | Gluf, Jr. | F16K 31/0637 137/270 |
| 8,118,054 | B2 * | 2/2012 | Glaudel | F16K 1/385 137/270 |
| 9,016,305 | B2 * | 4/2015 | Morris | F15B 13/0825 137/269 |

OTHER PUBLICATIONS

International Search Report for PCT/US2013/029561 data of mailing May 21, 2013.

\* cited by examiner

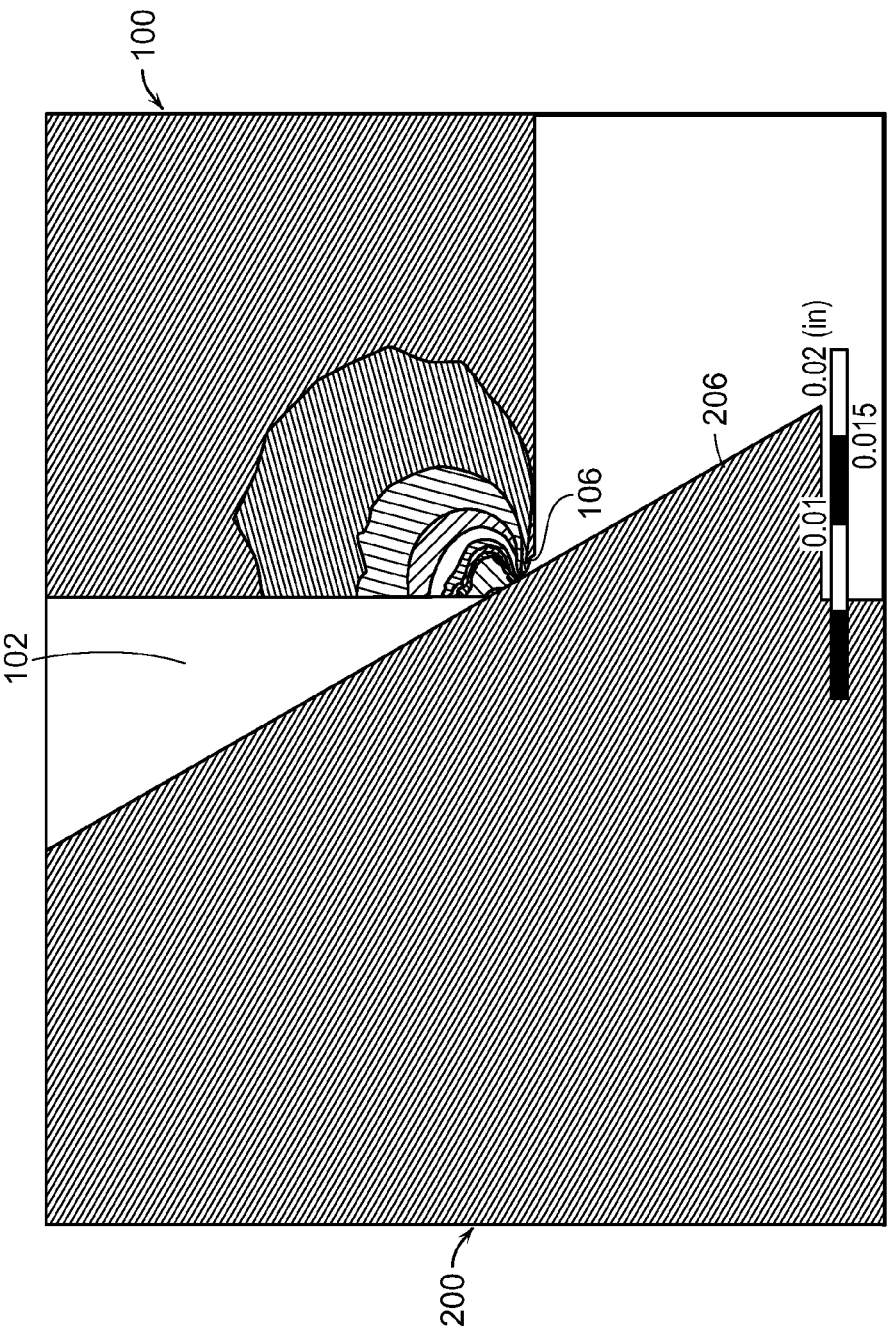

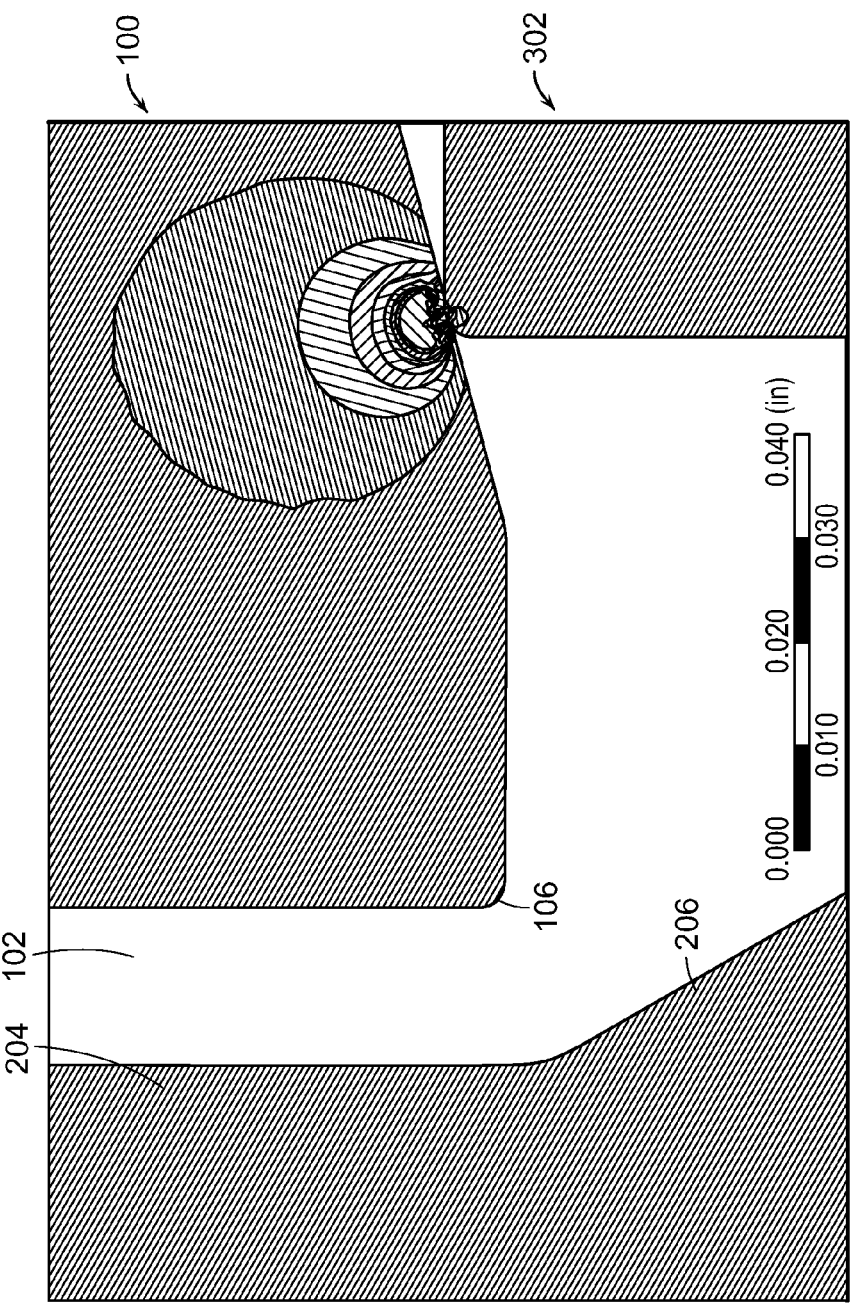

MODULAR SOLENOID VALVE KITS AND ASSOCIATED METHODS

RELATED APPLICATION

This application is a National Stage Application of International Application No. PCT/US2013/029561, filed Mar. 7, 2013, which claims priority to U.S. Provisional Application No. 61/607,952, filing date Mar. 7, 2012. Each of the foregoing applications is incorporated herein by reference in its entirety.

TECHNICAL FIELD

The present disclosure relates to modular solenoid valve kits and associated methods and, in particular, to modular solenoid valve kits with components adapted to be interchanged to create (i) a pull-through normally open valve, (ii) a pull-through normally closed valve, (iii) a push-in normally open valve, and (iv) a push-in normally closed valve.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used

SUMMARY

Exemplary embodiments of the present technology include modular solenoid valve kits and associated methods with components adapted to be interchanged to create (i) a pull-through normally open valve, (ii) a pull-through normally closed valve, (iii) a push-in normally open valve, and (iv) a push-in normally closed valve in a cost and time-efficient manner and capable of implementation in a variety of chromatography system conditions, in particular, in $CO_2$-based chromatography systems.

In accordance with embodiments of the present technology, exemplary modular solenoid valve kits and associated methods are provided, involving a valve body that includes a plurality of actuator section components and a plurality of head section components. The plurality of actuator head section components include a drive solenoid, a solenoid return spring, a stroke calibration collar and an actuator-to-head calibration collar. The plurality of head section components include a needle, a stem return spring, a seal and a seat. The plurality of actuator section components and the plurality of head section components are adapted to be interchanged to create (i) a pull-through normally open valve, (ii) a pull-through normally closed valve, (iii) a push-in normally open valve, and (iv) a push-in normally closed valve.

Interchanging the plurality of actuator section components and the plurality of head section components permits an alteration of at least a solenoid stroke, a solenoid return spring force, a pull-through needle and seat configuration, a push-in needle and seat configuration, an actuator to stem gap, a stem return spring force, a pressure assisted closure and a pressure assisted opening. The solenoid return spring force and the stem return spring force can be altered to accommodate a desired load in the valve body.

Embodiments of the exemplary modular solenoid valve kits and associated methods can include one or more of the following features. In certain embodiments, the needle includes a needle stem and a needle head. In addition, the needle can include a needle tip. In one or more embodiments, a needle head diameter is greater than a needle stem diameter. In one or more embodiments, a needle head diameter is also greater than a needle tip diameter. In one or more embodiments, a bore diameter of the seat is greater than the needle stem diameter. In one or more embodiments, the bore diameter is also greater than the needle tip diameter. The needle head can include at least one head groove on a needle head face. The needle stem can include at least one stem groove. The needle further includes an exterior coating of at least one of, e.g., a gold coating, a platinum coating, a ceramic coating, a polymer coating, or the like.

In one or more embodiments, the needle includes an angular sealing surface between the needle stem and the needle head for self-centering and aligning the needle during translation through the seat. A pull-through needle is implemented in a pull-through needle and seat configuration. In particular, the pull-through needle is configured to be pulled through the seat to stop flow through the bore of the seat. Pulling the needle through the seat to stop flow through the bore reduces an exposed volume of the valve body. The solenoid return spring of the pull-through normally open valve is configured to actuate to permit the stem return spring to pull the needle through the seat to stop flow through the bore of the seat. The angular sealing surface is pulled against a bore edge of the seat to stop flow through the bore. In general, plastic deformation of the bore edge occurs during pulling of the angular sealing surface against the bore edge and conforms the bore edge geometry to a complimentary angular sealing surface geometry. The plastic deformation of the bore edge geometry ensures a tight seal against the angular sealing surface. A pressure assist force can further enhance the tight seal against the angular sealing surface. The solenoid return spring of the pull-through normally closed valve is configured to actuate to push the needle through the seat to start flow through the bore of the seat.

In another exemplary embodiment, the needle includes an angular sealing surface between the needle head and the needle tip for self-centering and aligning the needle during translation into the seat. A push-in needle is implemented in a push-in needle and seat configuration. In particular, the push-in needle is configured to be pushed into the seat to stop flow through the bore of the seat. The solenoid return spring of the push-in normally open valve is configured to actuate to push the needle into the seat to stop flow through the bore of the seat. The angular sealing surface is pushed against a bore edge of the seat to stop flow through the bore. In general, plastic deformation of the bore edge occurs during pushing of the angular sealing surface against the bore edge and conforms the bore edge geometry to a complimentary angular sealing surface geometry. The plastic deformation of the bore edge geometry ensures a tight seal against the angular sealing surface. A pressure assist force can further enhance the tight seal against the angular sealing surface. The solenoid return spring of the push-in normally closed valve is configured to actuate to permit the stem return spring to pull the needle out of the seat to start flow through the bore of the seat. The seat can be fabricated from, e.g., a 30% carbon fiber filled PEEK material, a filled or unfilled grade PEEK material, a filled or unfilled grade of polyimide plastic, and the like. The polyimide plastic can be, e.g., Vespel® commercially available from E. I. du Pont de Nemours & Company, Wilmington, Del., USA.

In accordance with another embodiment of the present disclosure, exemplary methods of fabricating a modular solenoid valve are presented, involving providing a valve body that includes a plurality of actuator section components and a plurality of head section components. The plurality of actuator section components include a drive solenoid, a solenoid return spring, a stroke calibration collar and an actuator-to-head calibration collar. The plurality of head section components include a stem, a stem return spring, a seal and a seat. The exemplary method further includes interchanging the plurality of actuator section components and the plurality of head section components to create (i) a pull-through normally open valve, (ii) a pull-through normally closed valve, (iii) a push-in normally open valve, and (iv) a push-in normally closed valve.

The modular solenoid valve kits and associated methods of the present disclosure provide numerous advantages. For example, one or more embodiments of the present technology provide a kit of common components for any 2-way valve configuration. $CO_2$-based chromatography systems contain a plurality of differently configured and/or dimensioned valves for controlling the pressurization of the system. For implementation of a wide range of pressures, additional valves must be designed/selected and purchased, thereby increasing design/selection time and costs of the $CO_2$-based chromatography system. Embodiments described herein feature modular components adapted to be interchanged to create (i) a pull-through normally open valve, (ii) a pull-through normally closed valve, (iii) a push-in normally open valve, and (iv) a push-in normally closed valve. By utilizing the exemplary kits and associated methods in accordance with the present technology, solenoid valves for a pressurized system can be modified in a cost and time-efficient manner for implementation in a variety of $CO_2$-based chromatography system conditions.

BRIEF DESCRIPTION OF THE DRAWINGS

The foregoing and other features and advantages provided by the present disclosure will be more fully understood from the following description of exemplary embodiments when read together with the accompanying drawings, in which:

FIGS. 9A-C illustrate an exemplary embodiment of a pull-through needle with stem grooves and exemplary seat plastic deformation according to the present disclosure;

DESCRIPTION OF EXEMPLARY EMBODIMENTS

Figure 1:
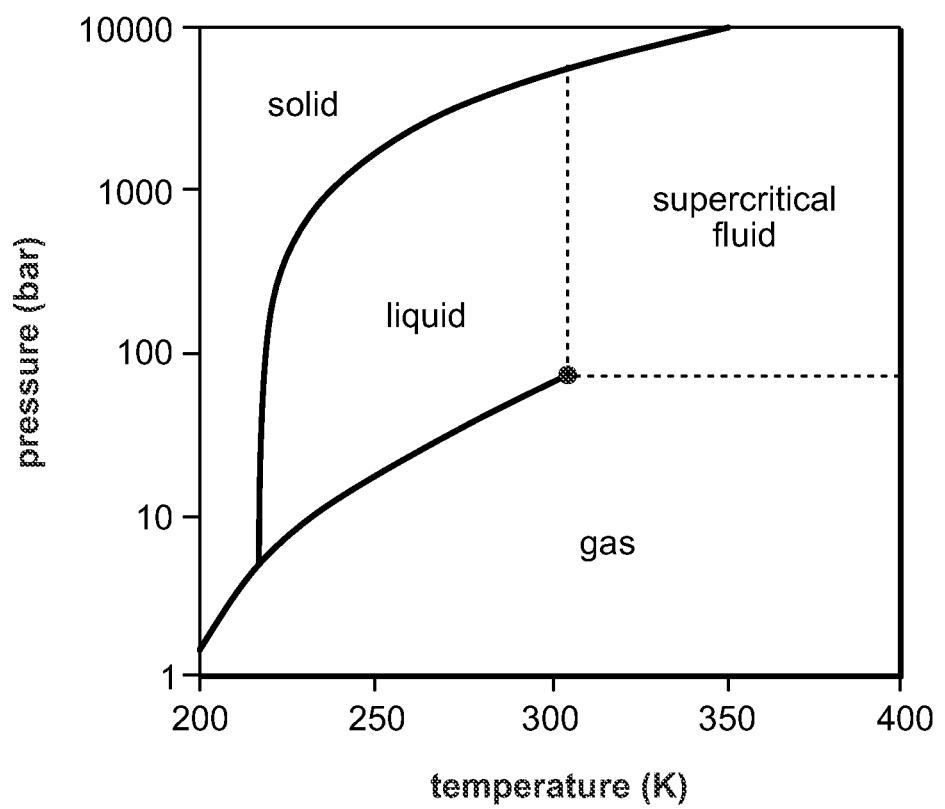
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

In general, conventional SFC systems include a plurality of valves, e.g., vent solenoid valve, shut-off solenoid valve, and the like, to control the flow and/or pressure of the system. The plurality of valves are generally configured and dimensioned differently relative to each other. Further, the plurality of valves are generally configured and/or sized for a particular system pressure or based on the desired unpowered or "normal" state of these conventional, prior art system. For example, a vent valve can be normally open to ensure the system is not pressurized when in an unpowered state. Thus, when an unpowered state of the system is desired or a different system pressure is to be implemented, additional valves must be designed/selected and purchased. The lengthy design/selection time and the increased costs of purchasing additional valves can result in substantially higher costs of conventional SFC systems.

Exemplary embodiments of the present technology are directed to modular solenoid valves, modular solenoid valve kits and associated methods that allow for kit components to be interchanged to create multiple different configurations of a two way valve. For example, the kits allow for modification of valves into one or more of the following configurations: (i) a pull-through normally open valve, (ii) a pull-through normally closed valve, (iii) a push-in normally open valve, and (iv) a push-in normally closed valve.

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
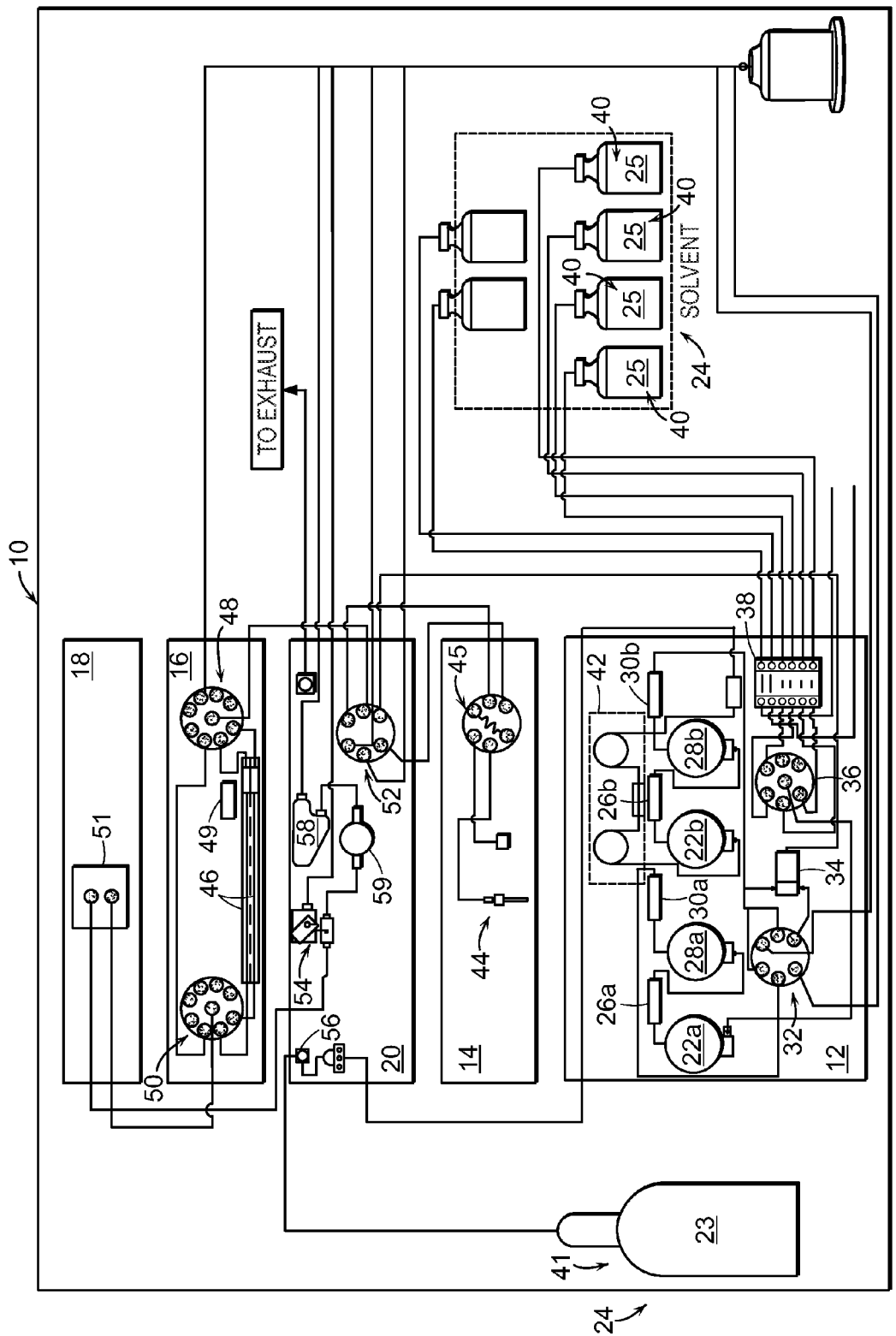
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10"). While the present embodiment is illustrative of a $CO_2$-based chromatography system 10 operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of the system 10, introduction of the sample to the mobile phase, separation of the sample into components, and/or detection of the sample components, as well as venting of the sample and/or mobile phase from the system 10.

Figure 3:
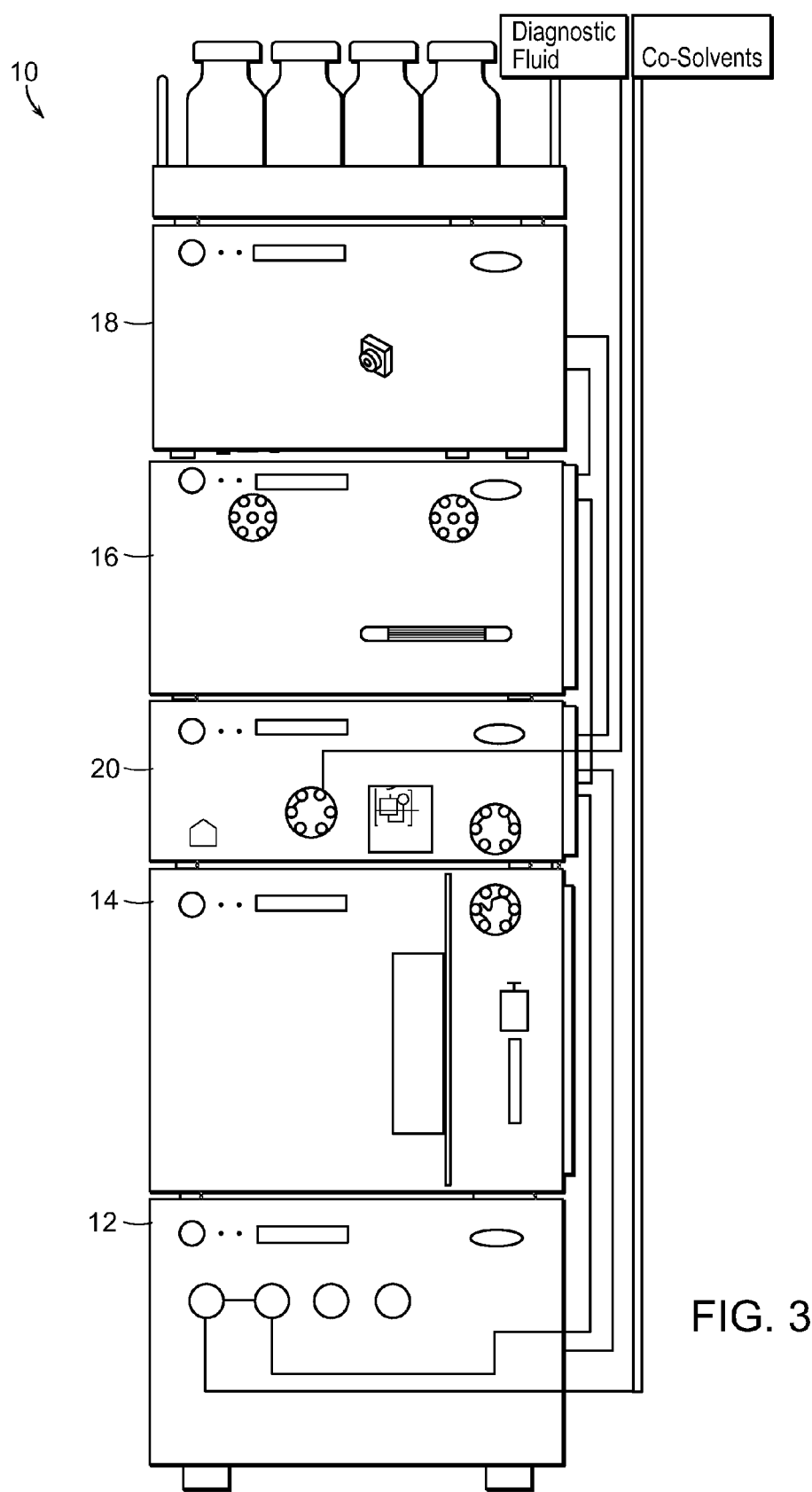
FIG. 3 is a block diagram of an exemplary arrangement of an embodiment of the system of FIG. 2.
Figure 4:
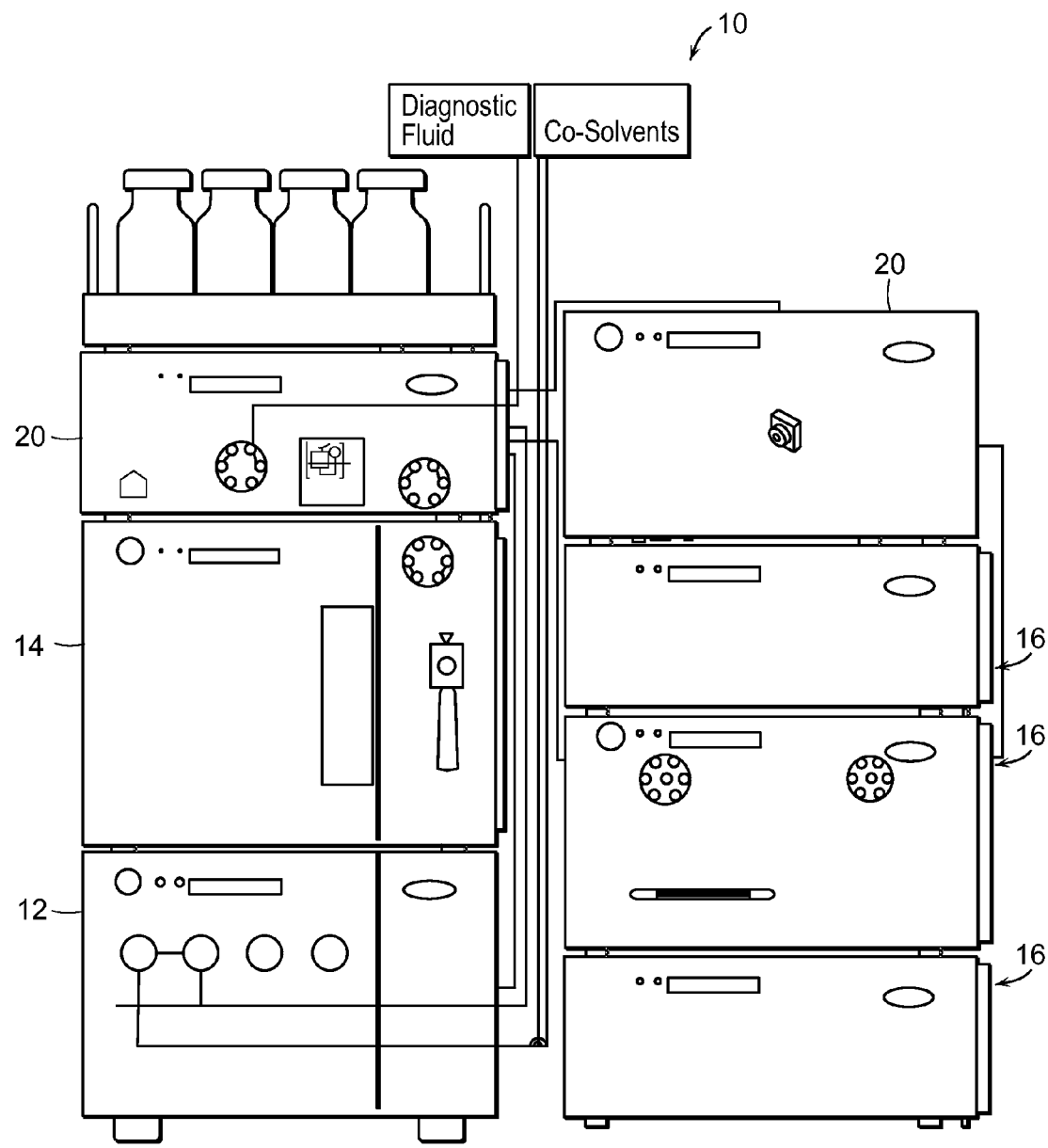
FIG. 4 is a block diagram of another exemplary arrangement of an embodiment of the system of FIG. 2.

In the present embodiment, the system 10 can include a solvent delivery system 12, a sample delivery system 14, a sample separation system 16, a detection system 18 (e.g., a PDA detector), and a system/convergence manager 20. In some embodiments, the system components can be arranged in one or more stacks. As another example, in one embodiment, the system components of the system 10 can be arranged in a single vertical stack (FIG. 3). The system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a and 22b configured to pump one or more solvents 24, such as mobile phase media 23 (e.g., carbon dioxide) and/or modifier media 25 (i.e., a co-solvent, such as, e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a and 26b can be configured to sense the pressure and/or flow rate associated with the output of the solvent 24 from the pumps 22a and 22b, respectively. Each pump 22a and/or 22b further includes a pump control valve configured to be actuated into, e.g., a flow position, a block position, a vent position, and the like.

The outputs of the pumps 22a and 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a and 30b can be configured to sense pressure and/or flow rate at an output of the accumulators 28a and 28b, respectively. The outputs of the accumulators 28a and 28b can be operatively coupled to a multiport valve 32, which can be controlled to vent the solvent 24 (e.g., mobile phase media 23 and modifier media 25) being pumped by the pumps 22a and 22b and/or to output the solvent 24 to a mixer 34. The mixer 34 can mix the modifier media 25 and the mobile phase media 23 output from the pumps 22a and 22b, respectively (e.g., after first passing through the accumulators 28a and 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent containers 40 such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent container 41 such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selectively receive an output from the one or more columns 46 and to pass the output of the selected one or more columns 46 to the detection system 18. The columns 46 can be removably disposed between the valves 48 and 50 to facilitate replacement of the one or more columns 46 to new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transitions from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut-off valve 56 can be configured to disconnect the solvent supply from the inlet of the pump 22b of the solvent delivery system to prevent the solvent from being pumped through the system 10. The vent valve 54 and the shut-off valve 56, e.g., solenoid valves, can be fabricated from the exemplary modular solenoid valve kits described in more detail below. In exemplary embodiments, the shut-off valve 56 can be incorporated into one or more pumps 22a and 22b or anywhere else in the system 10 if a controller is attached.

The back pressure regulator 58 can control the back pressure of the system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
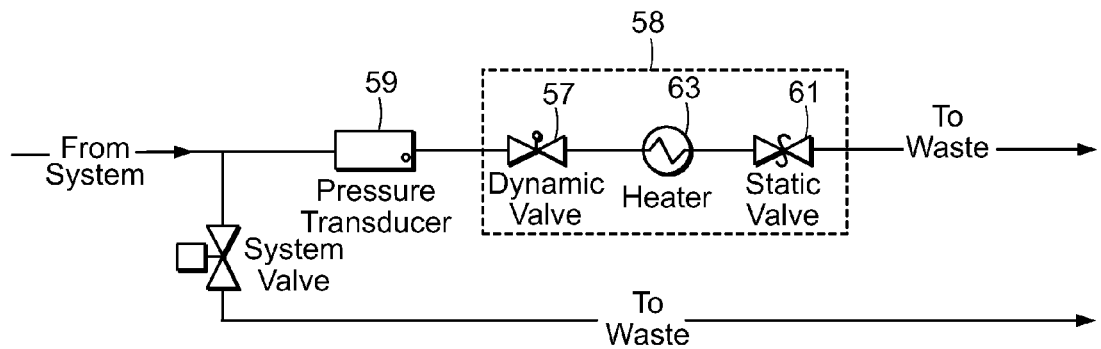
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator 61.

In summary, an exemplary operation of the system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems 10 which are amendable to preparatory methods and separations with high efficiency and correlation to analytical runs.

In accordance with embodiments of the present disclosure, exemplary modular solenoid valve kits and associated methods are provided, involving a valve body that includes a plurality of actuator section components and a plurality of head section components. The plurality of actuator head section components include a drive solenoid, a solenoid return spring, a stroke calibration collar and an actuator-to-head calibration collar. The plurality of head section components include a needle, a stem return spring, a seal and a seat. The plurality of actuator section components and the plurality of head section components are adapted to be interchanged to create (i) a pull-through normally open valve, (ii) a pull-through normally closed valve, (iii) a push-in normally open valve, and (iv) a push-in normally closed valve. In other embodiments, the exemplary modular solenoid valve kits can include additional needles and seats for creating a pull-through and/or push-in configuration and can further include additional solenoid return springs and stem return springs for implementation with different system pressures.

Figure 6:
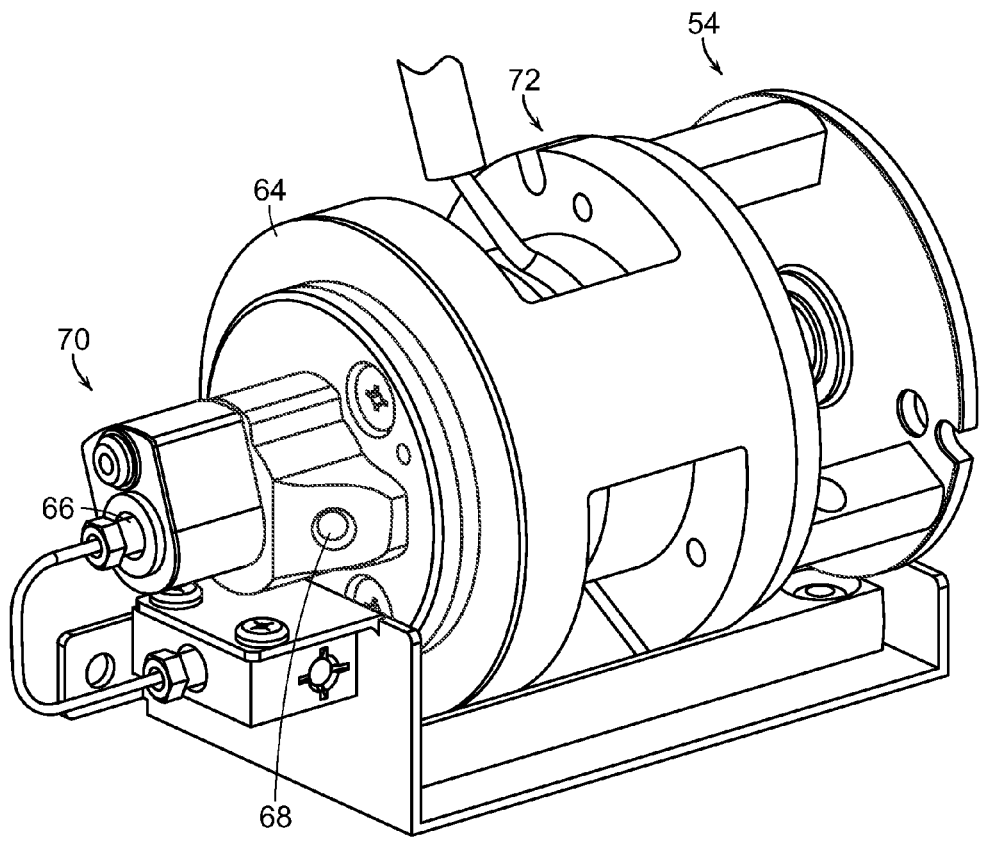
FIG. 6 is an exemplary embodiment of a solenoid valve according to the present disclosure.

With reference to FIG. 6, an exemplary solenoid valve 60 compiled from an exemplary modular solenoid valve kit is depicted, including a valve body 64, an inlet port 66 and an outlet port 68. The solenoid valve 60 can be, e.g., the vent valve 54, the shut-off valve 56, the back pressure regulator 58, a pressure relief valve, and the like. It should be understood that in exemplary embodiments, as will be discussed in detail below, the inlet port 66 can be the upstream portion, while the outlet port 68 can be the downstream portion, and vice versa. Further, at least one of the inlet port 66 and the outlet port 68 can be pressurized. For example, the vent valve 54 can include a pressurized inlet port 66 as the upstream portion and a non-pressurized outlet port 68 as the downstream portion. As a further example, the shut-off valve 56 can include a pressurized outlet port 68 as the upstream portion and a pressurized inlet port 66 as the downstream portion. Thus, the flow of the solvent 24 (e.g., mobile phase media 23) can be in either direction based on the configuration of the solenoid valve 60.

The solenoid valve 60 has two sections, i.e., an actuator section 72 and a head section 70. As will be discussed in greater detail below, the head section 70 includes the seat retainer, the stem return spring, the stem seal, the needle and the seat to be implemented in the exemplary solenoid valve 60. The actuator section 72 includes an actuator, i.e., a drive solenoid, a solenoid return spring, a solenoid stroke calibration collar, i.e., a stroke calibration collar, and a stem/solenoid calibration collar, i.e., an actuator-to-head calibration collar. The head section 70 and actuator section 72 components of the exemplary modular solenoid valve 60 kit are configurable and/or interchangeable to create at least one of (i) a pull-through normally open valve, (ii) a pull-through normally closed valve, (iii) a push-in normally open valve, and (iv) a push-in normally closed valve and can be calibrated for a specific system 10 pressure. Thus, the set of components of the modular solenoid valve 60 act as a platform to set up any configuration of a 2-way valve. It should be understood that the dimensions and/or configurations of the solenoid valve 60 are merely exemplary and other embodiments can have different dimensions and/or configurations.

Figure 7A:
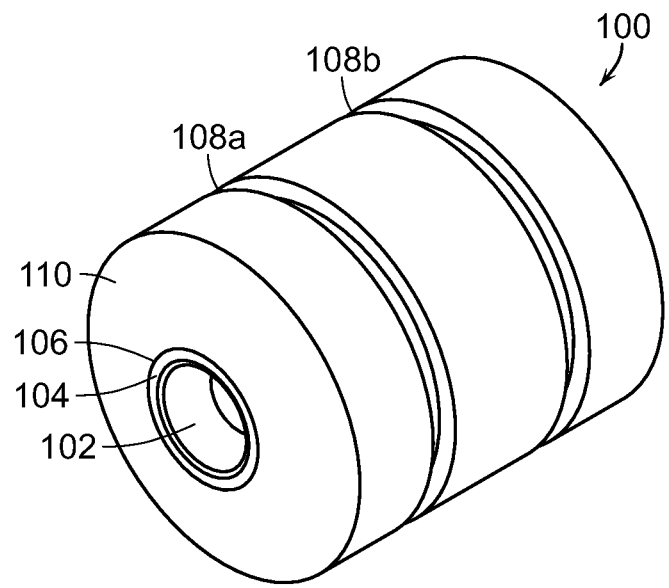
FIGS. 7A and 7B are exemplary embodiments of a seat for a pull-through solenoid valve according to the present disclosure.
Figure 7B:
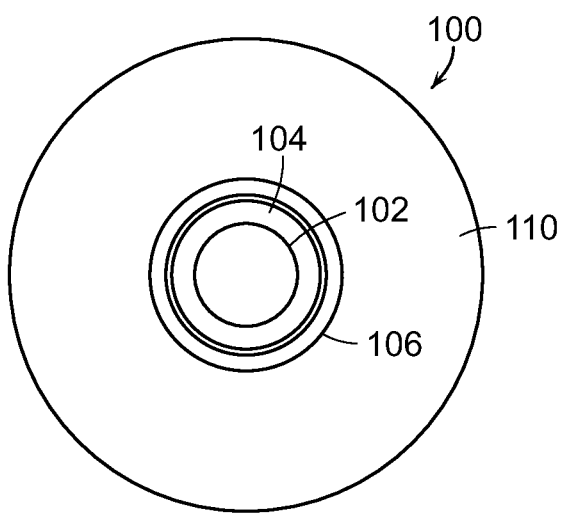

Turning to FIGS. 7A and 7B, an exemplary seat 100 for a pull-through solenoid valve 60 configuration is illustrated, including a bore 102 extending therethrough. It should be understood that in other embodiments, the seat 100 may be implemented in a push-in solenoid valve 60 configuration, i.e., rather than pulling a needle through the seat 100, a needle can be pushed into the seat 100 to stop flow through the bore 102. The bore 102 is greater in diameter than a needle stem diameter (or a needle tip diameter for a push-in configuration) to ensure the needle stem can pass through unimpeded. It should therefore be understood that the bore 102 dimension can differ based on the needle stem being implemented. The bore 102 can include a chamfered outlet 104, e.g., angled, beveled, outwardly sloping, and the like, to create a larger opening surface area than the bore 102 diameter for sealing against the needle head. For example, the chamfered outlet 104 can be at about, e.g., 15°, 20°, 25°, 30°, 35°, 40°, 45°, and the like. In other embodiments, the chamfered outlet 104 can be at an angle less than the taper of the angled sealing surface of the needle. For example, the chamfered outlet 104 angle can be half or less of the angle of the taper of the angled sealing surface of the needle. The larger opening surface area created by the chamfered outlet 104 can assist in centering and/or guiding the needle head as it is pulled into the bore 102. The edge adjoining the chamfered outlet 104 of the bore 102 and outer side surfaces 110 of the seat 100 can be defined by the bore edge 106.

The seat 100 may include circumferential seat grooves 108a and 108b to enhance the fastening of the seat 100 inside the seat retainer. In particular, an inner surface of the seat retainer can include protrusions, e.g., spikes, ridges, and the like, configured and dimensioned to mate with the seat grooves 108a and 108b. Thus, as the seat retainer is fastened and/or tightened around the seat 100 and/or the seat 100 is pressed into the seat retainer, the seat retainer protrusions can mate with the seat grooves 108a and 108b to prevent undesired motion of the seat 100 within the seat retainer. Although illustrated with two seat grooves 108a and 108b, other embodiments of the exemplary seat 100 can have less and/or more seat grooves 108a and 108b, e.g., zero, one, two, three, four, five, and the like.

Figure 8A:
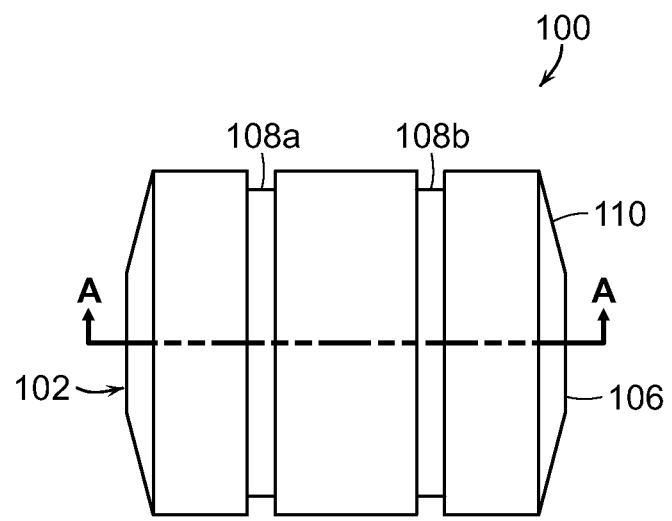
FIGS. 8A and 8B are side and cross-sectional views of exemplary embodiments of a seat for a pull-through solenoid valve according to the present disclosure.
Figure 8B:
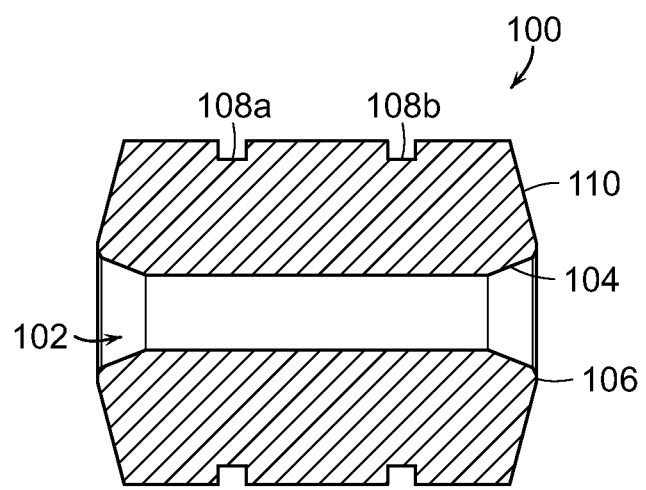

FIGS. 8A and 8B depict a side view and a cross-sectional side view, respectively, of the exemplary seat 100. In particular, FIG. 8B depicts a cross-sectional view of the seat 100 along plane "A". As can be seen, the bore 102 passes through the length of the seat 100 and the chamfered outlets 104 on both sides of the bore 102 increase the opening surface area at the outer side surfaces 110 to a surface area greater than the bore 102 diameter. The outer side surfaces 110 can be, e.g., angled, parallel to the seat grooves 108a and 108b, or the like. For example, in FIG. 8B, the outer side surfaces 110 define angled sides.

Figure 9A:
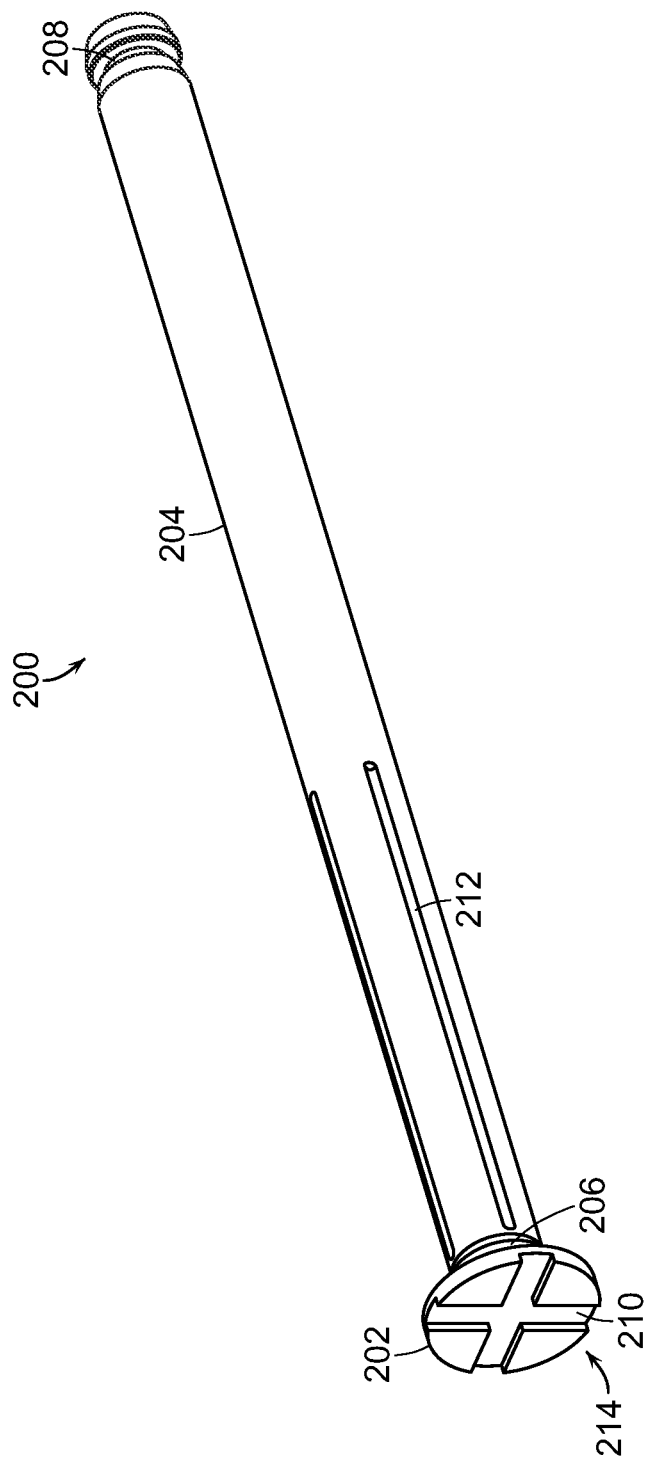

Turning now to FIG. 9A, an exemplary needle 200 is illustrated for a pull-through solenoid valve 60, including a needle head 202 and a needle stem 204. The diameter of the needle head 202 is greater than the diameter of the needle stem 204 to ensure a durable and/or tight seal can be created between the needle head 202 and the seat 100 when the needle stem 204 is pulled through the bore 102. The diameter of the needle stem 204 can be configured and dimensioned to pass unimpeded through the bore 102. In particular, the diameter of the needle stem 204 can be slightly smaller than the diameter of the bore 102 to permit the needle stem 204 to pass through the bore 102, while supporting the needle 200. Thus, no matter which dimensions and/or configurations of the needle 200 and/or seat 100 are being implemented, the diameter of the needle stem 204 will always be slightly smaller than the diameter of the bore 102.

The needle 200 includes an angular sealing surface 206 between the needle stem 204 and the needle head 202. In particular, the angular sealing surface 206 can act as a transition and/or connection area between the needle stem 204 and the needle head 202. The angular sealing surface 206 can be, e.g., sloping, convex, concave, or the like. Thus, when the needle stem 204 is pulled and/or translated through the bore 102 of the seat 100 to stop flow through the bore 102, the seat 100 can act as, e.g., a bushing, and the angular sealing surface 106 can self-center, e.g., align, guide, or the like, the needle 100 to ensure the needle head 202 is centered with respect to the bore 102. The needle 200 can further include an exterior coating of, e.g., gold, platinum, ceramic, polymer, and the like. The exterior coating can protect the needle 200 from, e.g., corrosion, pitting, and the like, caused by the system pressure loads and/or solvents involved during operation. The exterior coating can further protect the needle 200 from metal-to-metal contact with, e.g., the inlet port 66 when the solenoid valve 60 is actuated into an open position. For example, the needle head 202 can come in direct contact against a portion of the inlet port 66 (e.g., metal, in which the inlet port 66 is formed from) when the needle stem 204 has been translated through the bore 102 to create a flow path between the angular sealing surface 206 and the bore edge 106. Alternatively, rather than the entire needle 200 including the exterior coating, only the needle head 202 and/or the angular sealing surface 206 can include the exterior coating.

When the needle 200 is pulled through the seat 100, a durable and/or tight seal is created between the angular sealing surface 206 and at least one of the bore edge 106 and the chamfered outlet 104. With reference to FIG. 9A, upon initial contact of the angular sealing surface 206 and the bore edge 106, a plastic deformation of the bore edge 106 may occur. In particular, the plastic deformation can conform the bore edge 106 geometry to a complimentary angular sealing surface 206 geometry. For example, if the bore edge 106 is defined by a pointed junction between the outer side surface 110 and the chamfered outlet 104, the bore edge 106 can plastically deform to a, e.g., sloping, convex, concave, or the like, surface complimentary to the angular sealing surface 206. The plastic deformation, in general, occurs during the first mating between the angular sealing surface 206 and the seat 100. However, it should be understood that the plastic deformation may occur after the first mating between the angular sealing surface 206 and the seat 100. The material of fabrication, e.g., the modulus of elasticity and yield strength of the material of fabrication, for the seat 100 can be selected such that a plastic deformation only occurs at the bore edge 106 and does not continue to plastically deform during the lifetime of the seat 100. Upon the initial plastic deformation, the bore edge 106 surface complimentary to the angular sealing surface 206 ensures an enhanced seal between said elements. Thus, rather than a seal at a pointed junction between the bore edge 106 and the angular sealing surface 206, the larger contact and/or sealing surface area, i.e., the plastically deformed bore edge 106, reduces the chance of leakage through the seal. With reference to FIG. 9C, in other embodiments, the seat 100 can further yield and/or plastically deform when securely clamped in the seat retainer 302.

Still with reference to FIG. 9A, the exemplary needle 200 can include a keeper groove 208, e.g., an annular channel, at a distal end of the needle stem 204. The keeper groove 208 can be configured and dimensioned to mate with, e.g., a collar, bushing, washer, or the like, to securely attach the distal end of the needle stem 204 to a stem return spring mechanism. The needle face 214 of the needle head 202 can include a plurality of head grooves 210. Although illustrated with two perpendicularly positioned head grooves 210 in FIG. 9A, in other embodiments, the needle head 202 can include more and/or less head grooves 210, e.g., zero, one, two, three, four, five, and the like, positioned as, e.g., parallel, differently angled, or the like, head grooves 210. For example, the needle head 202 may not include head grooves 210 and would therefore be defined by a substantially flat needle face 214. As a further example, the needle head 202 may include four head grooves 210 positioned at about 45° relative to each other. The head grooves 210 can be configured and dimensioned to allow passage of the solvent 24 (e.g., mobile phase media 23) during venting through said grooves, over the needle head 202 and the angular sealing surface 206, through the bore 102 and out of the outlet port 68. In particular, the head grooves 210 can enhance the flow of the solvent 24 (e.g., mobile phase media 23) through the seat 100 by, e.g., reducing the flow resistance created by the needle head 202. Similarly, the needle stem 204 can include stem grooves 212 to enhance the flow of the solvent 24 (e.g., mobile phase media 23) through the bore 102. Although illustrated with four stem grooves 212 positioned at 90° angles relative to each other around the circumference of the needle stem 204, other embodiments can include more and/or less stem grooves, e.g., zero, one, two, three, four, five, six, and the like. In addition, the stem grooves 212 can extend, e.g., the entire length of the needle stem 204, a partial length of the needle stem 204, or the like.

Figure 10A:
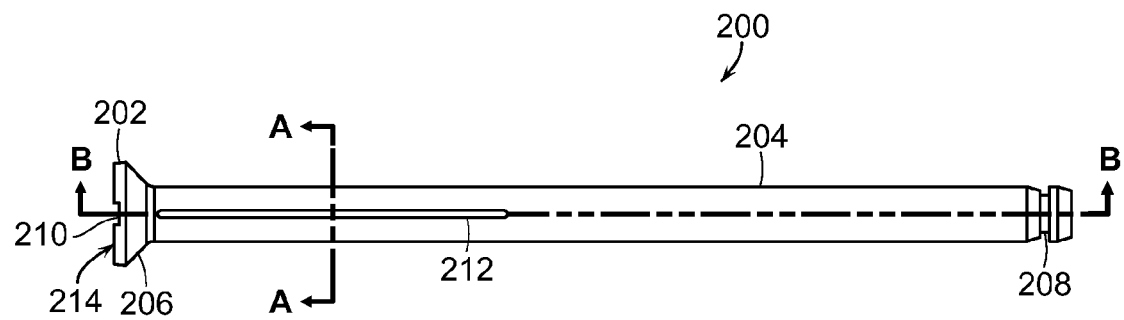
FIGS. 10A-D are side, cross-sectional and detailed views of an exemplary embodiment of a pull-through needle with stem grooves according to the present disclosure.
Figure 10B:
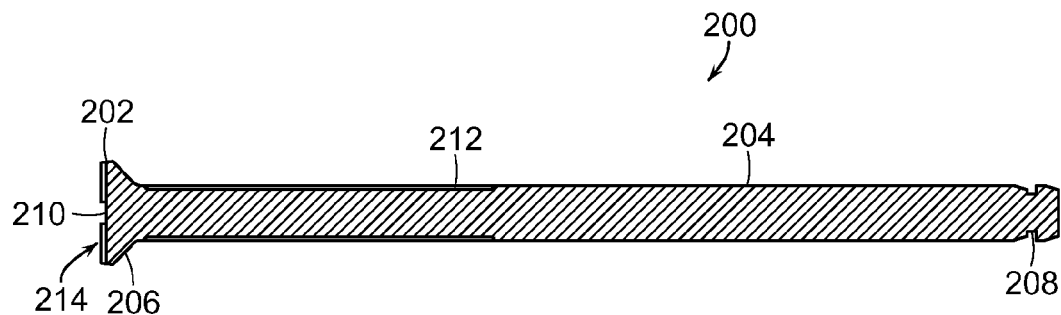

With respect to FIGS. 10A-D, cross-sectional, side and detailed views are provided of the exemplary needle 200. FIG. 10A illustrates a side view of the needle stem 200, including the angular sealing surface 206. In addition, FIG. 10A provides planes "A" and "B" for reference of the cross-sectional views of FIGS. 10B and 10C. The cross-sectional side view of the needle 200 is provided in FIG. 10B along plane "B". As can be seen, the stem grooves 212 create a channel in the needle stem 204. The dimensions of the stem grooves 212, e.g., the depth, width, length, or the like, can be altered as desired to provide a larger and/or smaller volumetric area for the flow of the solvent 24 (e.g., mobile phase media 23). It should be understood that a larger volumetric area of the stem grooves 212 results in a larger exposed volume of the vent valve which is required to be filled to reach a desired venting pressure level or to seal off the majority of the solenoid valve 60. Thus, an exemplary needle 200 in accordance with the present technology may have small and/or no stem grooves 212.

Figure 10C:
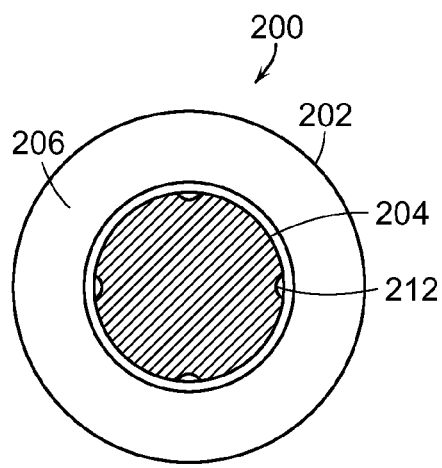
Figure 10D:
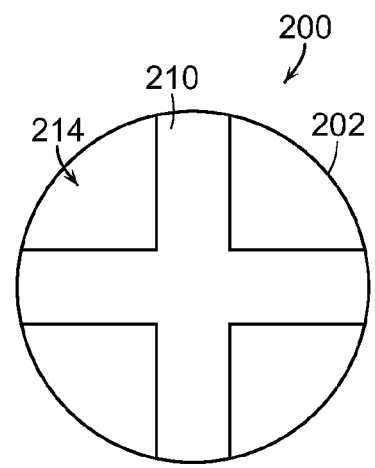

FIG. 10C is a cross-sectional view of the needle 100 along plane "A". In particular, the relationship between the needle head 202 diameter and the needle stem 204 diameter can be seen, i.e., the needle head 202 diameter is greater than the needle stem 204 diameter. In addition, the stem grooves 212 can be seen in the needle stem 204. With reference to FIG. 10D, a front view of the needle face 214 is provided. The needle face 214 can include head grooves 210, e.g., channels, passing across the entire needle face 214 to create a flow path for the solvent 24 (e.g., mobile phase media 23) when the solenoid valve 60 is actuated into an open position. It should be understood that once the pull-through configuration of the solenoid valve 60 is actuated into a closed position, i.e., the angular sealing surface 206 has been pulled against the seat 100, the solvent 24 (e.g., mobile phase media 23) cannot pass through the contact and/or sealing area of the angular sealing surface 206 and the bore edge 106.

Figure 11:
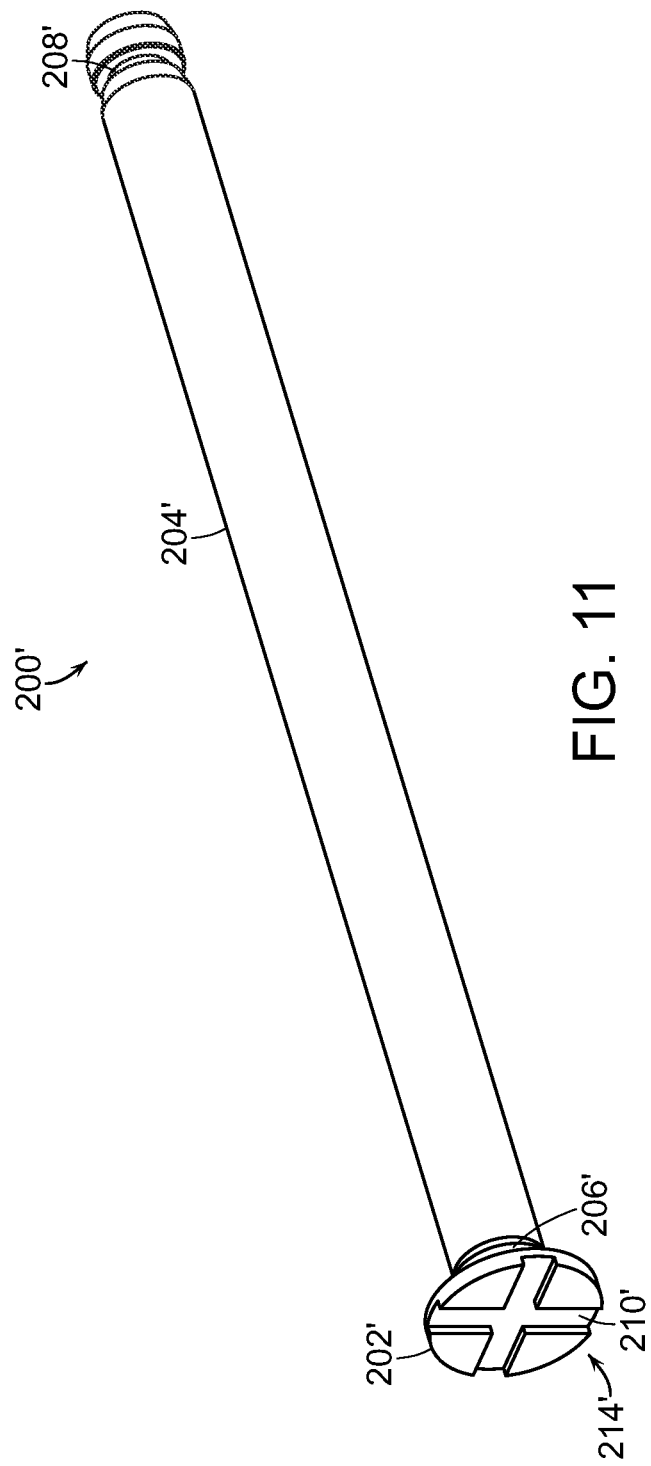
FIG. 11 is an exemplary embodiment of a pull-through needle without stem grooves according to the present disclosure.

Turning to FIG. 11, another exemplary embodiment of a needle 200' for a pull-through solenoid valve 60 is illustrated. The needle 200' is substantially similar to the needle 200 previously discussed, including a needle head 202', a needle stem 204' and a keeper groove 208' at a distal end of the needle stem 204'. Additionally, the needle 200' includes an angular sealing surface 206', i.e., a transition region, between the needle head 202' and the needle stem 204'. The needle face 214' of the needle head 202' can further include head grooves 210'. However, Similar to the needle face 214, it should be understood that in other embodiments, the needle face 214' can include more and/or less head grooves 210', e.g., zero, one, two, three, four, and the like. Rather than including stem grooves 212, the exemplary needle stem 204' can be defined by a uniformly dimensioned needle stem 204' surface.

Figure 12A:
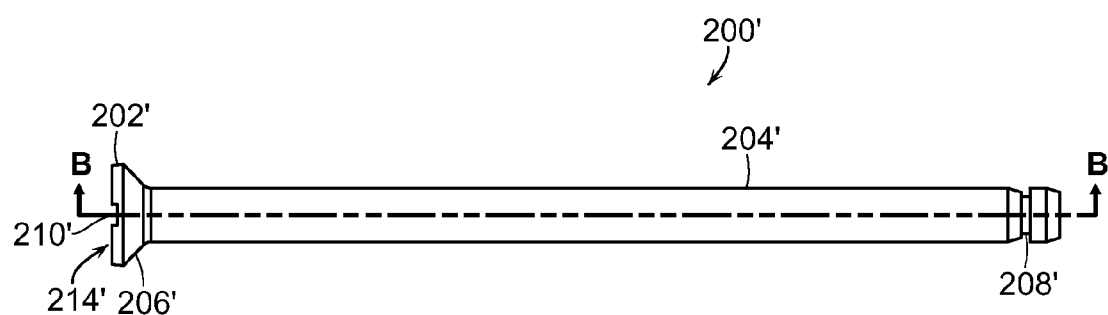
FIGS. 12A and 12B are side and cross-sectional views of an exemplary embodiment of a pull-through needle without stem grooves according to the present disclosure.
Figure 12B:
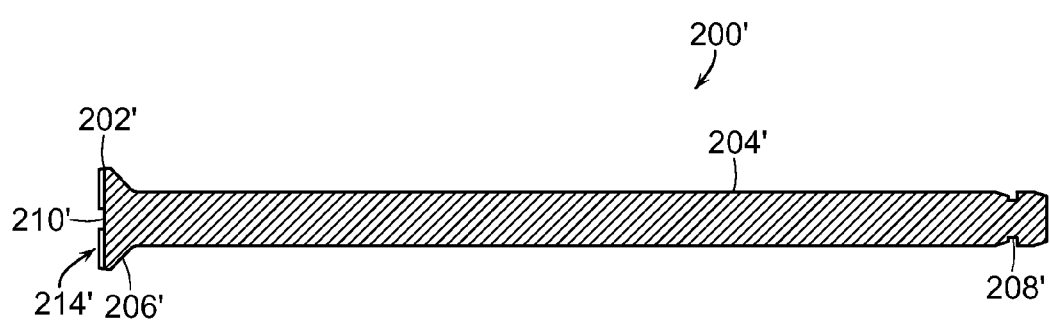

FIGS. 12A and 12B are side and cross-sectional views of the exemplary needle 200'. In particular, FIG. 12A depicts a side view of the needle 200' with a uniformly dimensioned needle stem 204', i.e., a needle stem 204' without stem grooves 212. Plane "B" is depicted as a reference for the cross-sectional view of FIG. 12B. As can be seen in the cross-sectional side view, the needle stem 204' is uniformly dimensioned along the entire length of the needle stem 204' between the keeper groove 208' and the angular sealing surface 206'. A rounded joint, e.g., a fillet, can further connect the angular sealing surface 206' and the needle stem 204'.

Figure 13A:
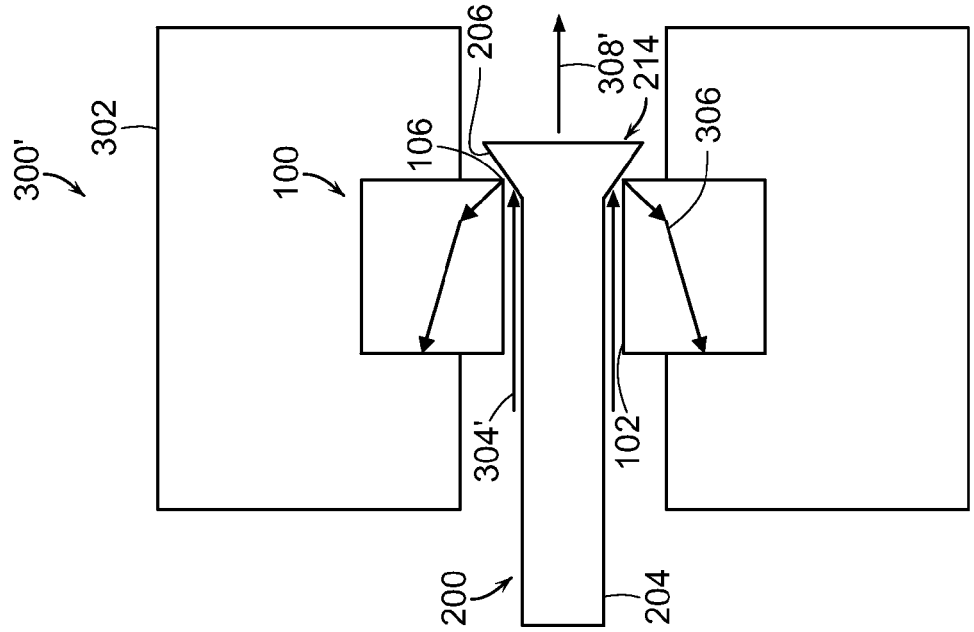
FIGS. 13A and 13B are exemplary embodiments of a seat retainer assembly illustrating a pressure assist according to the present disclosure.
Figure 13B:
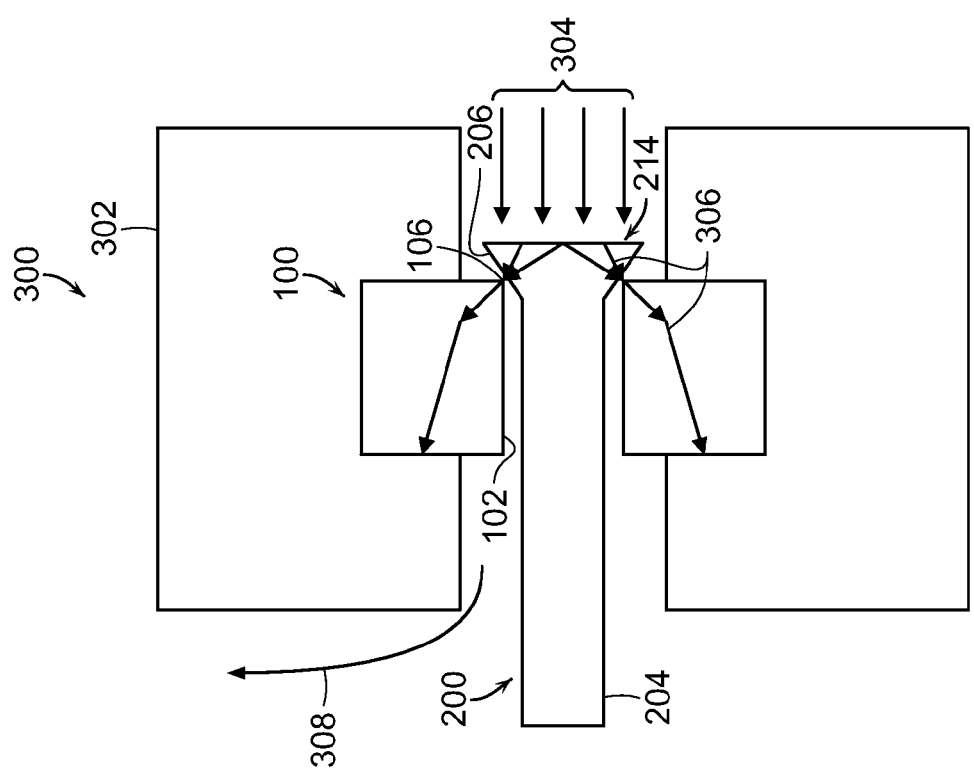

Turning now to FIGS. 13A and 13B, seat retainer assemblies 300 and 300' are depicted, including a seat retainer 302, a seat 100 and a needle 200. Although referring to a needle 200, it should be understood that the exemplary seat retainer assembly 300 can instead include a needle 200'. The seat retainer 302 can be securely disposed inside the head section 70 of FIG. 6. The seat 100 can be securely disposed inside the seat retainer 302. As described above, although not illustrated in FIGS. 13A and 13B, the seat grooves 108a and 108b can mate with protrusions, e.g., ridges, spikes, or the like, of the internal contact surface of the seat retainer 302 to prevent undesired movement of the seat 100 in the seat retainer 302. The needle stem 204 is at least partially disposed inside the bore 102 of the seat 100 and can be translated within the bore 102. The keeper groove 208 at the distal end of the needle stem 204 can be secured to a stem return spring mechanism (not shown).

With respect to FIG. 13A, flow of the solvent 24 (e.g., mobile phase media 23) can enter the seat retainer assembly 300 through the inlet port 66 and can proceed in the direction illustrated by inlet arrows 304. Although illustrated in a closed position, i.e., the angular sealing surface 206 is pressed against the bore edge 106, it should be understood that in an open position, an open flow path between the bore edge 106 and the angular sealing surface 206 is available for the solvent 24 (e.g., mobile phase media 23) to pass through unimpeded. The open flow path, i.e., annular gap, can be in the range of, e.g., about 0.005 to 0.010 inches. Thus, the solvent 24 (e.g., mobile phase media 23) can enter through the inlet port 66, flow over the needle face 214 and the angular sealing surface 206 into the bore 102, and can further vent and/or flow out of the outlet port 68 in the direction shown by the outlet arrow 308. As would be understood by those of skill in the art, rather than an open and/or unfilled bore 102 which creates a large exposed volume, the exemplary seat retainer assembly 300 includes a bore 102 with a needle stem 204 passing therethrough to reduce the exposed volume. The reduced exposed and/or internal volume within the bore 102 enhances the ability of a user to control the pressure in the solenoid valve 60 and, thus, the system 10. For example, in a closed position, the needle stem 204 passing through the bore 102 seals off the majority of the exemplary solenoid valve 60, thereby leaving only the volume of the inlet port 66 and the small actuation area between the inlet port 66 and the needle face 214 exposed to the system 10.

The exemplary pull-through needle 200 configuration of FIG. 13A further permits the use of a pressure assist from the system pressure to seal the angular sealing surface 206 against the bore edge 106 and/or the seat 100. In particular, to actuate the solenoid valve 60 into a closed position, the stem 204 can be pulled through the bore 102 in a downstream direction to press the angular sealing surface 206 against the bore edge 106 and/or the seat 100. As would be understood by those of skill in the art, the flow of the solvent 24 (e.g., mobile phase media 23) from the inlet port 66 enters the seat retainer assembly 300 as indicated by the inlet arrows 304. Thus, the solvent 24 (e.g., mobile phase media 23) creates a pressure force due to the pressure of the system 10 on the needle face 214. In particular, the added force created by the solvent 24 (e.g., mobile phase media 23) can be represented by Equation 1 below.

$$F = P \times SA \quad (1)$$

wherein F is the added closing force created by the solvent 24 (e.g., mobile phase media 23), P is the system pressure on the needle face 214, and SA is the needle 200/stem 100 sealed area, which can be further represented by Equation 2.

$$SA = \pi \times r^2 \quad (2)$$

wherein r is the seal radius, i.e., the radius of the contact seal between the angular sealing surface 206 and the bore edge 106. An adjustment of the seal radius and/or diameter can therefore vary the amount of pressure assist created by the system 10.

The pressure force on the needle face 214 assists in translating the needle stem 204 through the bore 102 and further assists in pressing and/or sealing the angular sealing surface 206 against the bore edge 106. The added pressure force on the needle face 214 is thereby supported through the sealing surface, i.e., the contact area between the bore edge 106 and the angular sealing surface 206, to enhance the seal and/or improve the sealing stress between said components.

As illustrated by the load path arrows 306, the sealing force created by pulling the needle 200 through the seat 100 in conjunction with the pressure assist force creates a pressure load which passes through the needle head 202, the needle face 214 and/or the angular sealing surface 206 and is further transmitted into the seat 100. In turn, the seat 100 transmits the pressure load into the seat retainer 302, which absorbs the pressure forces, thereby providing support for the seat 100 and the needle 200 and/or prevents transmission of the pressure forces to other components of the assembly.

It should be understood that, e.g., the diameter of the sealing surface, the diameter of the bore 102, the diameter of the bore edge 106, the chamfered edge 104, the diameter of the needle stem 204, the diameter of the needle face 214, and the like, can be configured and dimensioned to modify the pressure assist created by the system pressure, as was previously discussed with respect to Equations 1 and 2. For example, the diameter of the needle face 214 can be increased to create a larger surface area upon which the pressure forces act, thereby increasing the pressure assist and/or sealing the angular sealing surface 206 against the bore edge 106. In contrast, the diameter of the needle face 214 can be decreased to reduce the surface area upon which the pressure forces act, thereby decreasing the pressure assist and/or sealing the angular sealing surface 206 against the bore edge 106. The materials of fabrication of the needle 200 and the seat 100 can further be selected to prevent damage of said components when a pressure assist force is introduced against the needle face 214.

With respect to FIG. 13B, flow of the solvent 24 (e.g., mobile phase media 23) can enter the seat retainer assembly 300' through the outlet port 68 and can proceed in the direction illustrated by the inlet arrows 304'. Although illustrated in a closed position, i.e., the angular sealing surface 206 is pressed against the bore edge 106, it should be understood that in an open position, an open flow path between the bore edge 106 and the angular sealing surface 206 is available for the solvent 24 (e.g., mobile phase media 23) to pass through unimpeded. Thus, the solvent 24 (e.g., mobile phase media 23) can enter through the outlet port 68, flow through the bore 102, flow over the angular sealing surface 206 and over the needle face 214 and further vent and/or flow out of the inlet port 66 in the direction shown by the outlet arrow 308'. As would be understood by those of skill in the art, rather than an open and/or unfilled bore 102 which creates a large exposed volume, the exemplary seat retainer assembly 300 includes a bore 102 with a needle stem 204 passing therethrough to reduce the exposed volume. The reduced exposed and/or internal volume within the bore 102 enhances the ability of a user to control the pressure in the solenoid valve 60 and, thus, the system 10. For example, in a closed position, the needle stem 204 passing through the bore 102 seals off the majority of the exemplary solenoid valve 60, thereby leaving only the volume of the inlet port 66 and the small actuation area between the inlet port 66 and the needle face 214 exposed to the system 10.

The exemplary pull-through needle 200 configuration of FIG. 13B further permits the use of a pressure assist from the system pressure to actuate the solenoid valve 60 into an open position, i.e., create a flow path opening between the angular sealing surface 206 and the bore edge 106 and/or the seat 100. In particular, to actuate the solenoid valve 60 into a closed position, the stem 204 can be pulled through the bore 102 in an upstream direction to press the angular sealing surface 206 against the bore edge 106 and/or the seat 100. As would be understood by those of skill in the art, the flow of the solvent 24 (e.g., mobile phase media 23) from the outlet port 68 enters the seat retainer assembly 300' as indicated by the inlet arrows 304'. Thus, the solvent 24 (e.g., mobile phase media 23) creates a pressure force due to the pressure of the system 10 on the angular sealing surface 206 in the direction of the outlet arrow 308'. In particular, the exposed angular sealing surface 206 area on which the pressure force is provided by the system 10 is the net pressure area, as it is the area of the pressure not countered by pressure elsewhere on the needle 200.

The pressure force on the angular sealing surface 206 assists in translating the needle stem 204 through the bore 102 to create a flow path opening between the angular sealing surface 206 and the bore edge 106. Unlike the seat retainer assembly 300 which includes a pressure assist to increase the sealing force against the bore edge 106, the added pressure force on the angular sealing surface 206 of the exemplary seat retainer assembly 300' enhances the ability and/or timing for the solenoid valve 60 to actuate into an open position. As illustrated by the load path arrows 306 in FIG. 13B, the sealing force created by pulling the needle 200 through the seat 100 and against the bore edge 106 still creates a pressure load which passes through the seat 100 and is further transmitted into the seat retainer 302, which absorbs the pressure forces, thereby providing support for the seat 100 and the needle 200 and/or prevents transmission of the pressure forces to other components of the assembly.

Similar to the seat retainer assembly 300, it should be understood that, e.g., the diameter of the sealing surface, the diameter of the bore 102, the diameter of the bore edge 106, the chamfered edge 104, the diameter of the needle stem 204, the surface area of the angular sealing surface 206, and the like, can be configured and dimensioned to modify the pressure assist created by the system pressure. For example, the surface area of the angular sealing surface 206 inside the bore 102, i.e., the stem/seat sealing diameter, can be increased to create a larger surface area upon which the pressure forces act in a closed position. As a further example, the diameter of the needle stem 204 can be changed to vary the pressure forces during actuation of the solenoid valve 60 in an open position.

Figure 14:
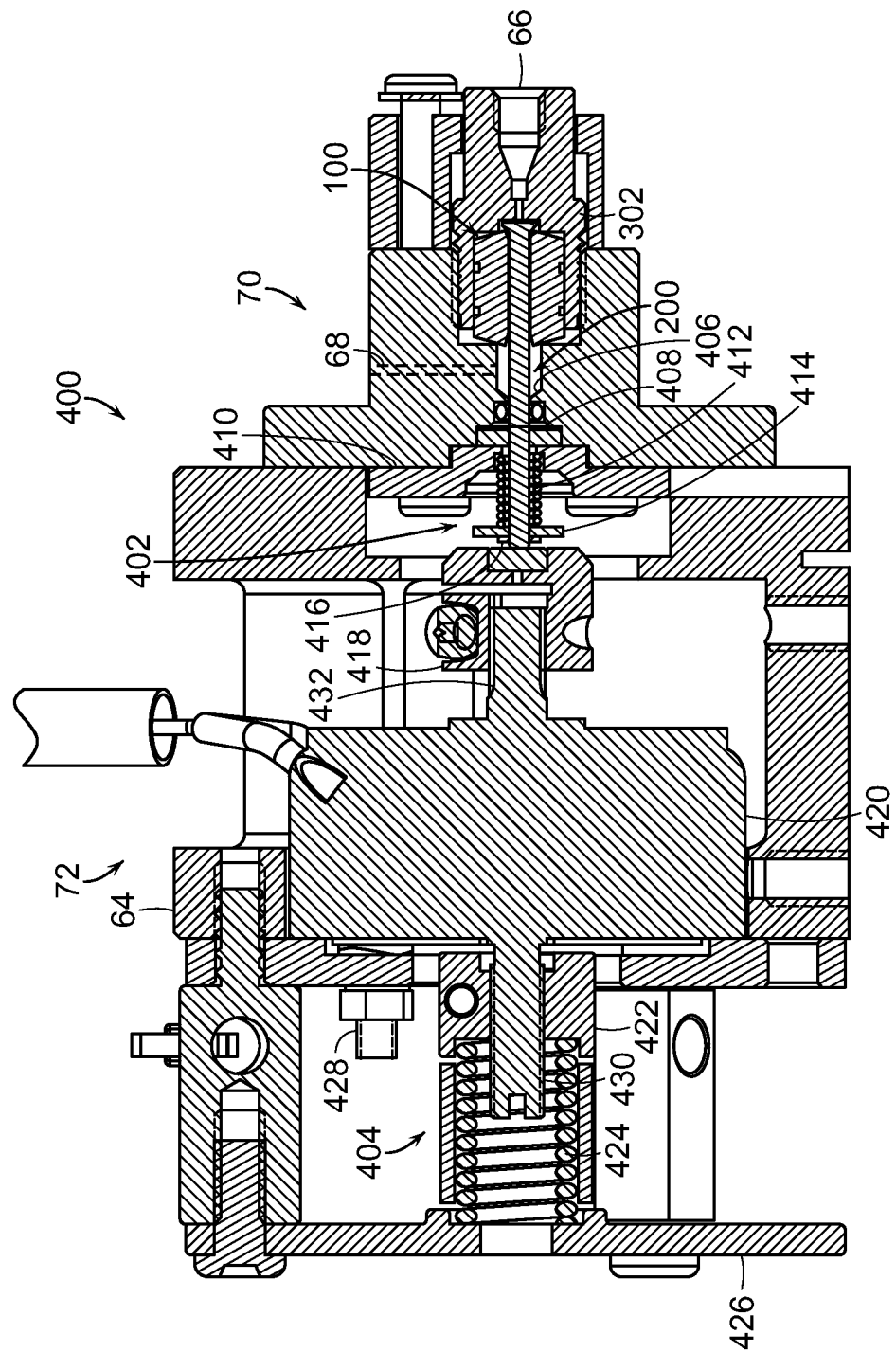
FIG. 14 is an exemplary embodiment of a pull-through solenoid valve in an open position according to the present disclosure.

Turning now to FIG. 14, an exemplary embodiment of a pull-through solenoid valve 400 is depicted in an open position, i.e., a flow path exists between the angular sealing surface 206 of the needle 200 and the bore edge 106 of the seat 100. The solenoid valve 400 includes a valve body 64, which includes an actuator section 72 and a head section 70. The seat retainer assembly 300 is securely disposed inside the head section 70, including the seat retainer 302, the seat 100 and the needle 200. The head section 70 further includes the inlet port 66 and the outlet port 68.

A stem return spring mechanism 402 disposed inside the valve body 64 includes, e.g., a stem return spring 412, a collar 414 and a retaining ring 416. The stem return spring mechanism 402 is securely connected to a distal end of the needle stem 204 with respect to the needle head 202. The collar 414 and the retaining ring 416 have an inner bore dimensioned to fit around the needle stem 204. In particular, the collar 414 can be securely fastened to the retaining ring 416, which in turn can be securely mounted around the needle stem 204 in the keeper groove 208. The retaining ring 416 may be configured and dimensioned to "snap" fit into the keeper groove 208. The retaining ring 416 can be, e.g., an O-ring, which snaps into the keeper groove 208. Alternatively, a spring pin and a hole in the needle stem 204 can be implemented. In other embodiments, alternative low profile axial retaining mechanisms known in the art may be used. The stem return spring 412 can be disposed around the needle stem 204 and can provide pressure directly against the collar 414 and a stem return spring plate 410. The stem return spring plate 410 is securely fastened to the valve body 64. The needle stem 204 further translates through a bore in the stem return spring plate 410.

The stem return spring 412 can be compressed by applying a compression force on the distal end of the needle stem 204 and, thereby, the collar 414, in the direction of the stem return spring plate 410. The motion of compressing the stem return spring 412 actuates the solenoid valve 400 into an open position. In particular, as the stem return spring 412 is compressed, the needle stem 204 translates through the bore 102 and creates a flow path opening between the angular sealing area 206 and the bore edge 106. As should be understood by those of skill in the art, when the stem return spring 412 is in a compressed state between the stem return spring plate 410 and the collar 414, the mechanical energy stored in the stem return spring 412 provides an expansion force against said components to expand the stem return spring 412 to its natural length. When the stem return spring 412 expands, the force against the collar 414 and the stem return spring plate 410 translates the needle stem 204 through the bore 102 in a direction away from the stem return spring plate 410. The solenoid valve 400 is thereby actuated into a closed position, i.e., the stem return spring 412 pulls the needle stem 204 through the bore 102 sufficiently to provide a sealing stress between the angular sealing surface 206 and the bore edge 106. Based on the upstream and downstream configuration of the solenoid valve 60, the pressure assist previously discussed either enhances the sealing stress, i.e., the sealing force, on the seal or enhances the ability of the solenoid valve 400 to actuate into an open position.

On a side opposing the stem return spring 412, the stem return spring plate 410 can include a stem seal 408, e.g., an ACQUITY BSM seal, securely disposed around the needle stem 204 and between the stem return spring plate 410 and the valve body 64 (see, e.g., Waters Technologies Corporation, Massachusetts, Mass., Head Plunger Seal, Product Number 700002599 (2011)). The stem seal 408 can ensure a waterproof and/or pressure resistant seal between the head section 70 and the return spring mechanism 402 and/or the actuator section 72, e.g., to prevent leakage of the solvent 24 (e.g., mobile phase media 23) through the bore in which the needle stem 204 is situated. Further, the head section 70 includes a cavity 406 into which the solvent 24 (e.g., mobile phase media 23) flows after passing through the bore 102. The stem seal 408 ensures that the solvent 24 (e.g., mobile phase media 23) flowing into the cavity 406 creates a pressure sufficient to vent and/or force the solvent 24 (e.g., mobile phase media 23) out of the solenoid valve 400 through the outlet port 68.

Still with reference to FIG. 14, the actuator section 72 includes the solenoid return spring mechanism 404 which further includes a solenoid return spring 424, a solenoid stroke calibration collar 422, a stem/solenoid calibration collar 418 (i.e., an actuator-to-head calibration collar) and an actuator 420 (i.e., a drive solenoid). In other embodiments, for a push-in normally open and/or a pull-through normally closed configuration of the solenoid valve 60, the actuator 420 can be flipped and a spring washer inside the actuator 420 can be implemented as a return spring.

The solenoid stroke calibration collar 422, as shown in FIG. 14, is securely fastened to a rear shaft 430 of the actuator 420. The solenoid stroke calibration collar 422 and the rear shaft 430 of the solenoid can be, e.g., threaded, or the like, to permit a calibration and/or adjustment of the position of the solenoid stroke calibration collar 422 and/or the "stroke" along the rear shaft 430. The solenoid stroke calibration collar 422 can further include a clamping feature for enhanced adjustment along and/or attachment to the rear shaft 430. Thus, the compression and/or expansion forces produced by the solenoid return spring 424 can be adjusted for a desired system pressure being implemented. The solenoid return spring 424 is disposed around the rear shaft 430 and between the solenoid stroke calibration collar 422 and a solenoid return spring plate 426. Further, the solenoid return spring 424 can be securely attached to the solenoid stroke calibration collar 422 and/or the solenoid return spring plate 426. The solenoid return spring plate 426 is securely mounted to the valve body 64. Thus, the solenoid return spring 424 can be compressed and/or expanded between the solenoid return spring plate 426 and the solenoid stroke calibration collar 422. As would be understood by those of skill in the art, a compression and/or expansion of the solenoid return spring 424 transmits the compression and/or expansion force to the solenoid stroke calibration collar 422, which in turn translates the actuator 420 towards and/or away from the solenoid return spring plate 426. An actuator guide protrusion 428 can pass through a bore of the valve body 64 and can assist in guiding the actuator 420 along an even and/or straight path. Although illustrated with one actuator guide protrusion 428, it should be understood that a greater and/or lesser number of actuator guide protrusions 428 can be implemented, e.g., zero, one, two, three, four, or the like.

A collar protrusion 432 extending from an actuator 420 side opposing the solenoid return spring 424 is utilized for attachment of the stem/solenoid calibration collar 418. The collar protrusion 432 and the stem/solenoid calibration collar 418 can be, e.g., threaded, or the like, to permit a calibration and/or adjustment of the position of the stem/solenoid calibration collar 418 along the collar protrusion 432. The stem/solenoid calibration collar 418 can further include a clamping feature for enhanced adjustment along and/or attachment to the collar protrusion 432. Thus, the distance of translation of the stem/solenoid calibration collar 418 can be adjusted for a desired system pressure being implemented. The stem/solenoid calibration collar 418 is in communication with the stem return spring mechanism 402. In particular, the stem/solenoid calibration collar 418 can, e.g., provide and/or remove a force against the distal end of the needle stem 204 to translate the needle stem 204 through the bore 102 to actuate the solenoid valve 400 into one of an open position and a closed position, respectively.

Figure 15:
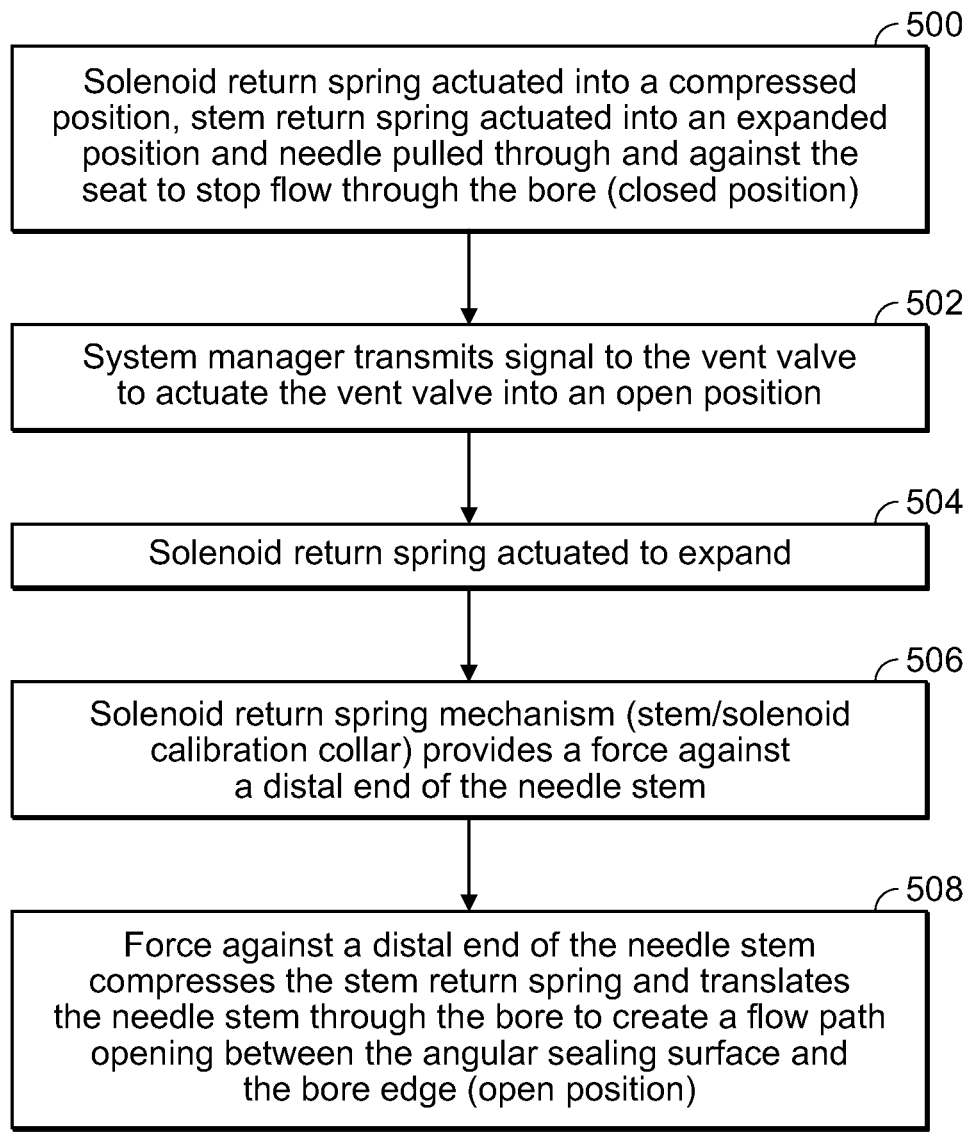
FIG. 15 is a block diagram for actuating an exemplary embodiment of a pull-through normally closed solenoid valve into an open position according to the present disclosure.

The exemplary solenoid valve 400 can be configured as one of a pull-through normally closed valve or a pull-through normally open valve. With respect to the pull-through normally closed valve and the block diagram of FIG. 15, the spring constants for the stem return spring 412 and the solenoid return spring 424 can be adjusted and/or selected according to the operational pressure to ensure that the stem return spring 412 is normally expanded and the solenoid return spring 424 is normally actuated into a compressed position (500). Alternatively, the solenoid can be flipped to disengage from the head section 70 when the solenoid valve 400 has been actuated into a closed position. As discussed previously, the expanded setting of the stem return spring 412 provides an expansion force against the stem return spring plate 410, which in turn pulls the needle stem 204 through the bore 102 to actuate the solenoid valve 400 into a closed position, i.e., the angular sealing surface 206 of the needle head 202 is pulled tightly against the bore edge 106 of the seat 100 to stop flow through the bore 102 (500). The compressed setting of the solenoid return spring 424 translates and/or retracts the actuator 420 and the stem/solenoid calibration collar 418 in a direction away from the stem return spring mechanism 402. Thus, the stem/solenoid calibration collar 418 does not provide a force against the distal end of the needle stem 204 when the solenoid return spring 424 is compressed. The system/convergence manager 20, discussed previously, is in communication with the solenoid valve 400 and can transmit a signal to the solenoid valve 400 to expand the solenoid return spring 424 to actuate the solenoid valve 400 into an open position (502). As would be understood by those of skill in the art, when the solenoid return spring 424 is actuated to expand (504), the expansion force generates a force by the stem/solenoid calibration collar 418 against the distal end of the needle stem 204 (506). The spring constant of the solenoid return spring 424 can be selected such that the force generated against the distal end of the needle stem 204 is sufficient to overcome the expansion force of the stem return spring 412. Thus, as the solenoid return spring 424 expands, the stem return spring 412 is compressed and the needle stem 204 is translated through the seat 100 to create an opening between the angular sealing surface 206 and the bore edge 106, i.e., the solenoid valve 400 is actuated into an open position (508).

Figure 16:
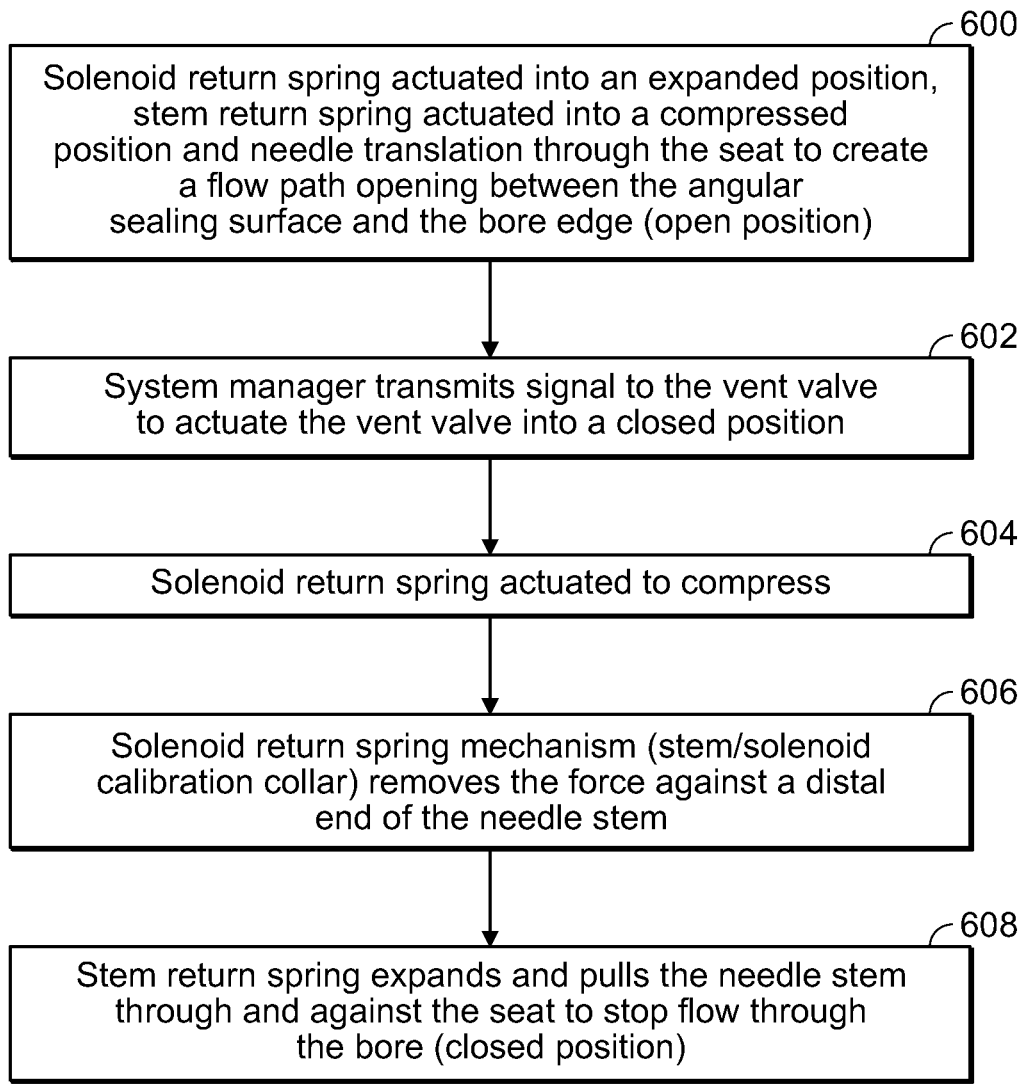
FIG. 16 is a block diagram for actuating an exemplary embodiment of a pull-through normally open solenoid valve into a closed position according to the present disclosure.

With respect to the pull-through normally open valve and the block diagram of FIG. 16, the spring constants for the stem return spring 412 and the solenoid return spring 424 can be adjusted and/or selected according to the operational pressure to ensure that the stem return spring 412 is normally compressed and the solenoid return spring 424 is normally actuated into an expanded position (600). As discussed previously, the expanded setting of the solenoid return spring 424 translates the actuator 420 and the stem/solenoid calibration collar 418 in the direction of the stem return spring mechanism 402. Thus, the stem/solenoid calibration collar 418 provides a force against the distal end of the needle stem 204 when the solenoid return spring 424 is expanded, causing the stem return spring 412 to compress. In particular, the spring constant of the solenoid return spring 424 can be selected such that it overcomes the spring constant of the stem return spring 412. The compressed setting of the stem return spring 412, in conjunction with the force on the distal end of the needle stem 204, provides a pulling force on the collar 414, which in turn translates the needle stem 204 through the bore 102 to actuate the solenoid valve 400 into an open position, i.e., a flow opening exists between the angular sealing surface 206 of the needle head 202 and the bore edge 106 of the seat 100 to permit flow through the bore 102 (600). The system/convergence manager 20, discussed previously, is in communication with the solenoid valve 400 and can transmit a signal to the solenoid valve 400 to compress the solenoid return spring 424 to actuate the solenoid valve 400 into a closed position (602). As would be understood by those of skill in the art, when the solenoid return spring 424 is actuated to compress (604), the force on the distal end of the needle stem 204 by the stem/solenoid calibration collar 418 is removed (606). The spring constant of the stem return spring 412 can be selected such that when the force generated against the distal end of the needle stem 204 is removed, the stem return spring 412 can automatically expand to close the solenoid valve 400. Thus, as the solenoid return spring 424 compresses, the stem return spring 412 expands and translates the collar 414 in a direction away from the stem return spring plate 410, thereby pulling the needle stem 204 through the seat 100 to create a durable and/or tight seal between the angular sealing surface 206 and the bore edge 106, i.e., the solenoid valve 400 is actuated into a closed position (608).

As discussed previously and now illustrated below in Table 1, a pressure assist from the system 10 can either enhance the sealing stress, i.e., the sealing force, on the seal or enhances the ability of the solenoid valve 400 to actuate into an open position based on the upstream and downstream configuration of the pull-through solenoid valve 400. The "Solenoid Actuation" is the directional actuation of the solenoid return spring 424 to open or close the solenoid valve 400, i.e., the solenoid return spring 424 compresses away from the seat 100 to close the solenoid valve 400 and expands toward the seat 100 to open the solenoid valve 400. The "Seat Port" indicates the port of entry of the solvent 24 (e.g., mobile phase media 23) into the solenoid valve 400, i.e., inlet indicating entry through the inlet port 66 and outlet indicating entry through the outlet port 68. The "Seat/Seal Diameters" is the relationship between the sealing diameter of the needle stem 204 and seat seal 408, i.e., the seal diameter, and the sealing diameter of the angular sealing surface 206 to the bore edge 106, i.e., the seat diameter. The area associated with these diameters determines the pressure load on the needle 200. For example, if the pull-through needle 200 is pressurized from the inlet port 66, the load on the needle face 214 is the pressure times the sealed cross-sectional area of the needle face 214, i.e., $$\frac{\pi d^2}{4},$$

wherein d is the diameter of the needle face 214. The "Normal Condition" indicates whether the solenoid valve 400 is normally open or normally closed. The "Pressure Assist Action (closed)" and "Pressure Assist Action (open)" specify the direction of the pressure assist load due to pressure in the closed and open conditions, respectively. Thus, if the pressure assist is close for the "Pressure Assist Action (closed)", the pressure assist adds an additional force to closing the solenoid valve 400. In contrast, if the pressure assist is open for the "Pressure Assist Action (closed)", the pressure assist adds an additional force to open the solenoid valve 400.

TABLE 1

Pull-Through Modular Solenoid Valve Configurations and Resulting Behaviors

| | Configuration | | | Behavior | |
|---|---|---|---|---|---|
| No. | Solenoid Actuation | Seat Port | Seat/Seal Diameters | Normal Condition | Pressure Assist Action (closed) | Pressure Assist Action (open) |
| 1 | Away from seat | Inlet | Seat > Seal | Open | Close | Close |
| 2 | Away from seat | Outlet | Seat > Seal | Open | Open | Close |
| 3 | Toward seat | Inlet | Seat > Seal | Closed | Close | Close |
| 4 | Toward seat | Outlet | Seat > Seal | Closed | Open | Close |

In the first exemplary configuration, the solenoid valve 400 is a pull-through normally open solenoid valve 400 with the solvent 24 (e.g., mobile phase media 23) entering the solenoid valve 400 through the inlet port 66. The solenoid return spring 424 actuates away from the seat 100 to close the solenoid valve 400. It should be noted that the "seat diameter", i.e., the sealing diameter of the angular sealing surface 206 to the bore edge 106, is greater than the "seal diameter", i.e., the sealing diameter of the needle stem 204 and seat seal 408, for each of the pull-through configurations. The pressure assist created by the entry of the solvent 24 through the inlet port 66 provides a force on the needle face 214 and further assists in closing the solenoid valve 400 in both the closed and open positions.

In the second exemplary configuration, the solenoid valve 400 is a pull-through normally open solenoid valve 400 with the solvent 24 entering the solenoid valve 400 through the outlet port 68. The solenoid return spring 424 also actuates away from the seat 100 to close the solenoid valve 400. The pressure assist created by the entry of the solvent 24 through the outlet port 68 and through the bore 102 against the angular sealing surface 206 creates an additional force to open the solenoid valve 400 in the closed position. However, the pressure assist created by the entry of the solvent 24 through the outlet port 68 and through the bore 102 against the angular sealing surface 206 creates an additional force to close the solenoid valve 400 in the open position.

In the third exemplary configuration, the solenoid valve 400 is a pull-through normally closed solenoid valve 400 with the solvent 24 entering the solenoid valve 400 through the inlet port 66. The solenoid return spring 424 actuates toward the seat 100 to open the solenoid valve 400. The pressure assist created by the entry of the solvent 24 through the inlet port 66 provides a force on the needle face 214 and further assists in closing the solenoid valve 400 in both the closed and open positions.

In the fourth exemplary configuration, the solenoid valve 400 is a pull-through normally closed solenoid valve 400 with the solvent 24 entering the solenoid valve 400 through the outlet port 68. The solenoid return spring 424 actuates toward the seat to open the solenoid valve 400. The pressure assist created by the entry of the solvent 24 through the outlet port 68 and through the bore 102 against the angular sealing surface 206 creates an additional force to open the solenoid valve 400 in the closed position. However, the pressure assist created by the entry of the solvent 24 through the outlet port 68 and through the bore 102 against the angular sealing surface 206 creates an additional force to close the solenoid valve 400 in the open position.

Figure 17:
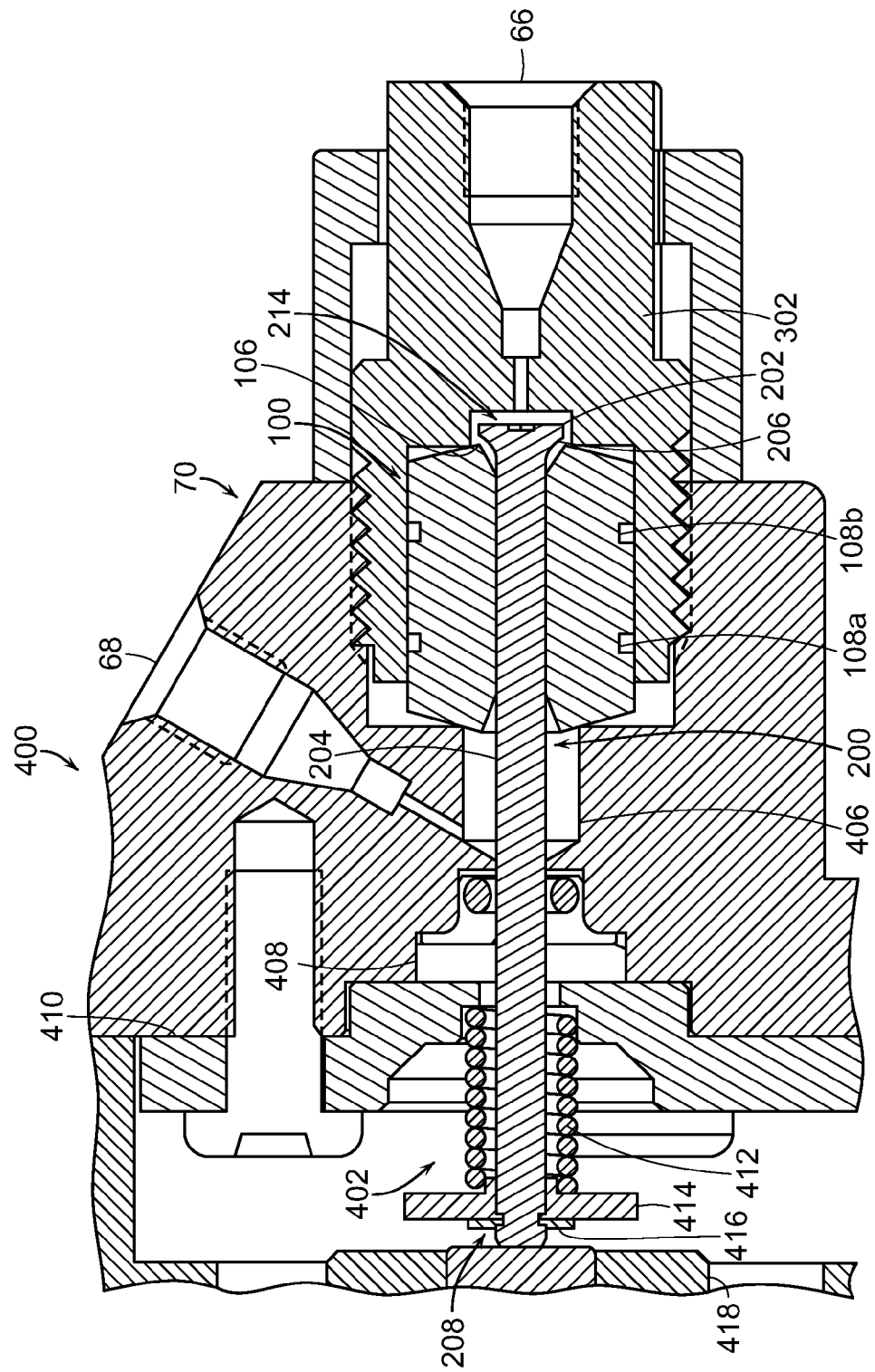
FIG. 17 is a detailed view of an exemplary embodiment of a pull-through solenoid valve in an open position according to the present disclosure.

Turning now to FIG. 17, a detailed cross-sectional view of the exemplary pull-through solenoid valve 400 is provided with specific focus on the head section 70 in an open configuration. The seat 100 is securely disposed inside the seat retainer 302. The seat retainer 302 can be securely fastened inside the head section 70 by, e.g., matching threading on an outer surface of the seat retainer 302 and an inner surface of the valve body 64. The solenoid valve 400 is illustrated actuated into an open position, i.e., a flow path exists between the angular sealing surface 206 and the bore edge 106.

Figure 18:
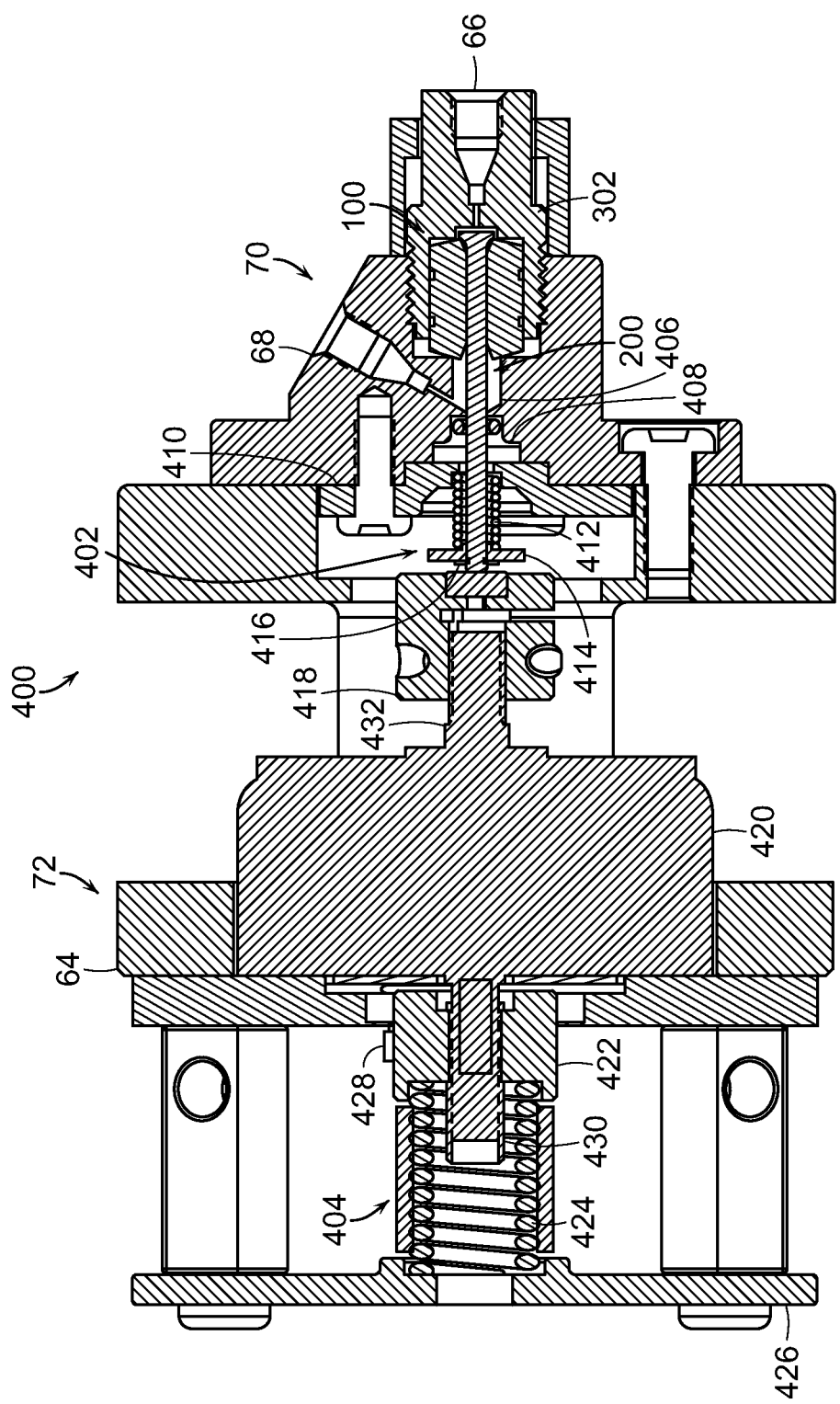
FIG. 18 is an exemplary embodiment of a pull-through solenoid valve in a closed position according to the present disclosure.

With reference now to FIG. 18, an exemplary embodiment of the pull-through solenoid valve 400 is depicted in a closed position, i.e., a durable and/or tight seal is created between the angular sealing surface 206 of the needle 200 and the bore edge 106 of the seat 100. The components of the solenoid valve 400 of FIG. 18 are substantially similar in configuration and/or function as those described with respect to the solenoid valve 400 of FIGS. 14 and 17. However, the actuation of the solenoid valve 400 of FIG. 18 into a closed position actuates the solenoid return spring mechanism 404 to permit the stem return spring mechanism 402 to pull the needle 200 through the seat 100 to stop flow through the bore 102. In particular, as the stem return spring mechanism 402 pulls the needle 200 through the seat 100, a durable and/or tight waterproof seal is created between the angular sealing surface 206 of the needle 200 and the bore edge 106 of the seat 100.

Figure 19:
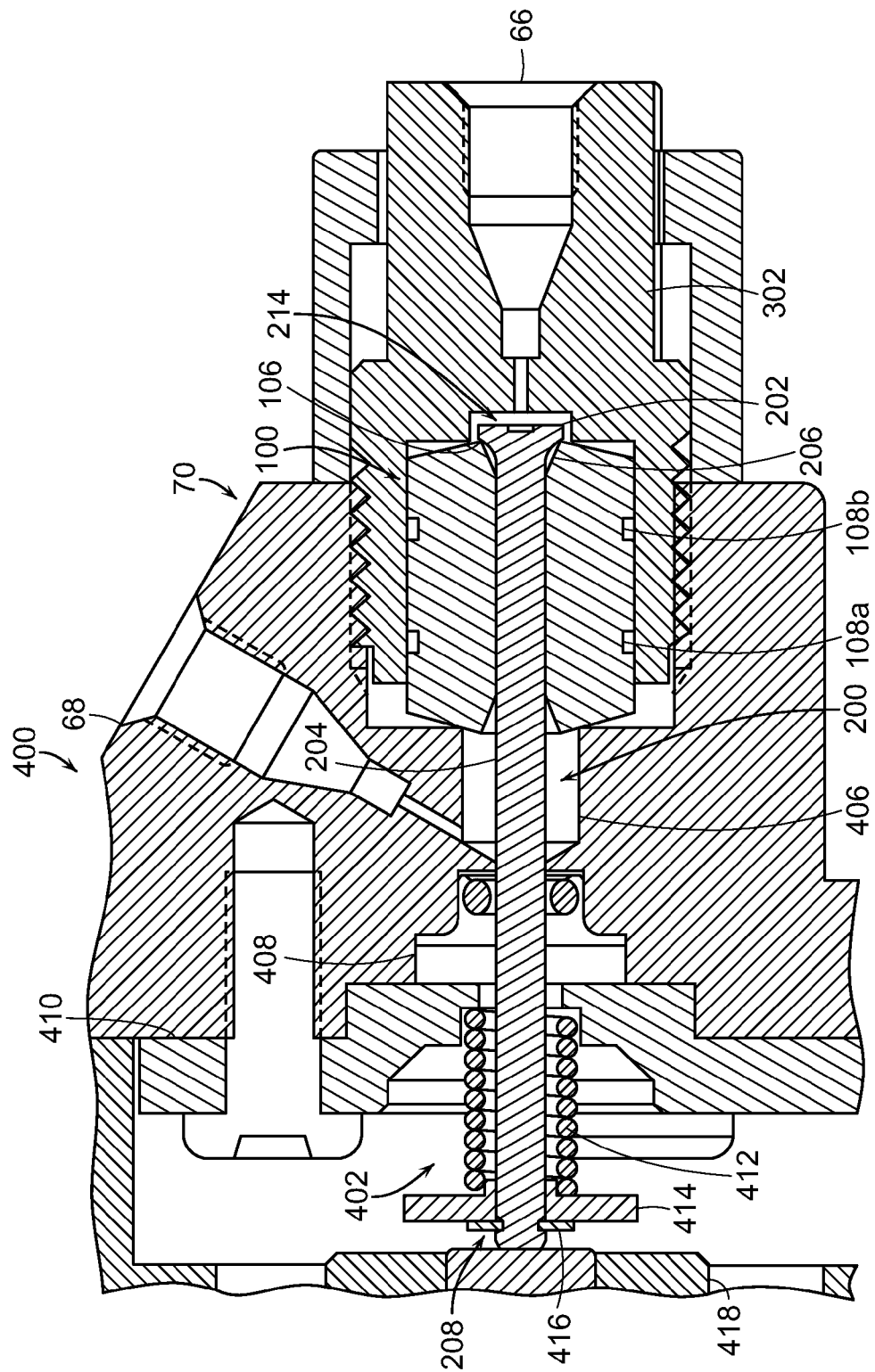
FIG. 19 is a detailed view of an exemplary embodiment of a pull-through solenoid valve in a closed position according to the present disclosure.

FIG. 19 is a detailed cross-sectional view of the exemplary pull-through solenoid valve 400, with specific focus on the head section 70 in a closed configuration. As previously discussed, the closed configuration and/or position is created by actuating the solenoid return spring mechanism 404 to permit the stem return spring mechanism 402 to pull the needle 200 through the seat 100 to stop flow through the bore 102. The durable and/or tight waterproof seal between the angular sealing surface 206 and the bore edge 106 prevents leakage of the solvent 24 (e.g., mobile phase media 23) therebetween.

As should be understood by those of ordinary skill in the art, the modularity of the head section 70 and the actuator section 72 components permits a user to create a variety of pull-through and/or push-in solenoid valve 60 configurations. For example, the modular solenoid valve 60 kit can include different configurations of the seats, needles and stem and solenoid return springs which can be interchanged to create the desired solenoid valve 60 configuration.

Figure 20A:
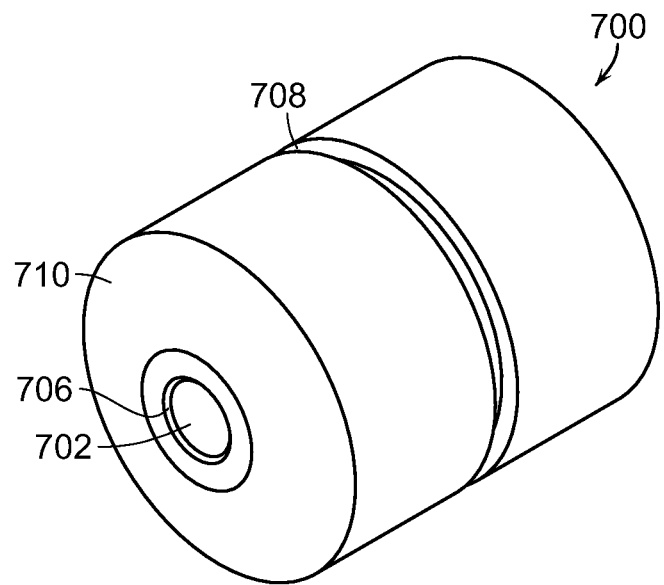
FIGS. 20A and 20B are exemplary embodiments of a seat for a push-in solenoid valve according to the present disclosure.
Figure 20B:
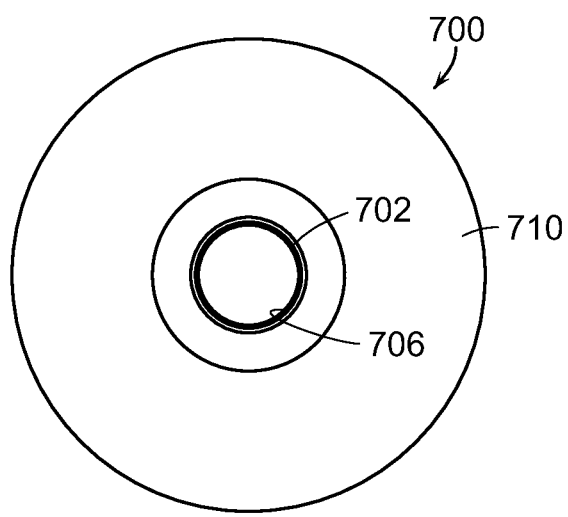

Turning now to FIGS. 20A and 20B, an exemplary seat 700 for a push-in solenoid valve 60 configuration is illustrated, including a bore 702 extending therethrough. It should be understood that in other embodiments, the seat 700 may be implemented in a pull-through solenoid valve 60 configuration, i.e., rather than pushing a needle into the seat 700, the needle 200 can be pulled through the seat 100 to stop flow through the bore 702, so long as a well-defined taper is implemented along the expanded sealing diameter for the pull-through needle 200. The bore 702 diameter is greater in diameter than a needle tip diameter (or a needle stem diameter for a pull-through configuration) to ensure the needle tip can pass through unimpeded. It should therefore be understood that the bore 702 dimension can differ based on the needle tip being implemented. The exemplary seat 700 can be substantially similar to the seat 100. However, rather than including a chamfered outlet 104, the seat 700 includes a continuous bore 702 diameter throughout the entire length of the seat 700. The edge adjoining the bore 702 and the outer side surfaces 710 of the seat 700 can be defined by a bore edge 706.

The seat 700 may include a circumferential seat groove 708 to enhance the fastening of the seat 700 inside the seat retainer. In particular, an inner surface of the seat retainer can include protrusions, e.g., spikes, ridges, and the like, configured and dimensioned to mate with the seat groove 708. Thus, as the seat retainer is fastened and/or tightened around the seat 700 and/or the seat 700 is pressed into the seat retainer, the seat retainer protrusions can mate with the seat groove 708 to prevent undesired motion of the seat 700 within the seat retainer. Although illustrated with one seat groove 708, other embodiments of the exemplary seat 700 can have less and/or more seat grooves 708, e.g., zero, one, two, three, four, five, and the like.

Figure 21A:
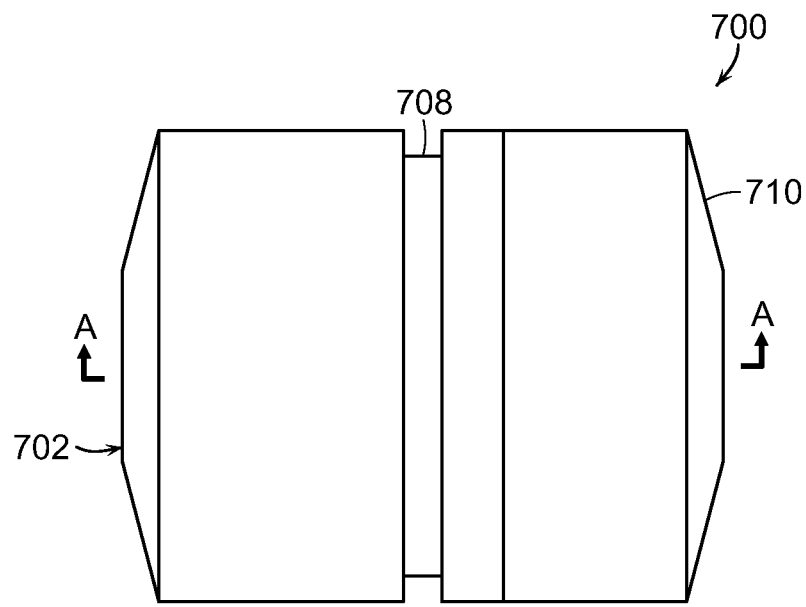
FIGS. 21A and 21B are side and cross-sectional views of exemplary embodiments of a seat for a push-in solenoid valve according to the present disclosure.
Figure 21B:
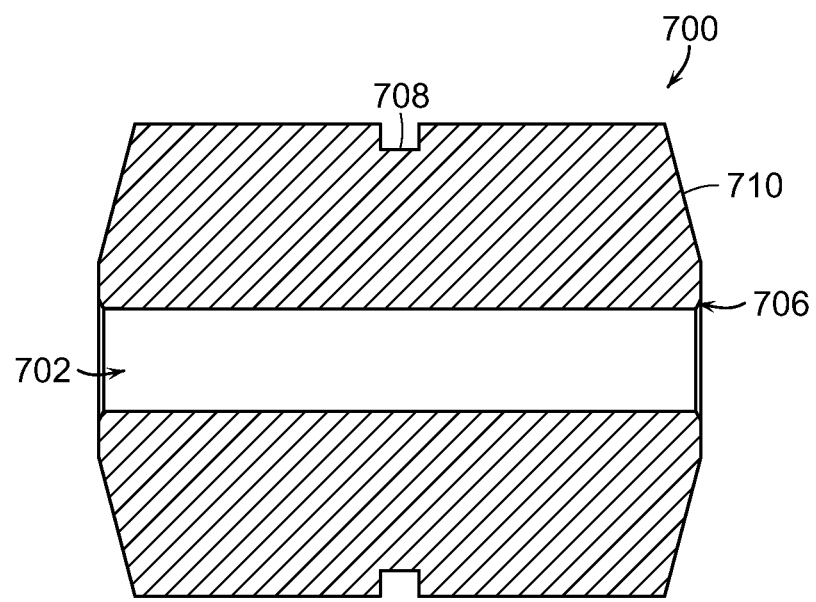

FIGS. 21A and 21B depict a side view and a cross-sectional view, respectively, of the exemplary seat 700. In particular, FIG. 21B depicts a cross-sectional view of the seat 700 along plane "A". As can be seen, the bore 702 passes through the length of the seat 700 and the junction between the bore 702 and the outer side surfaces 710 defines the bore edge 706. The outer side surfaces 710 can be, e.g., angled, parallel to the seat groove 708, or the like. For example, in FIG. 21B, the outer side surfaces 710 define angled sides.

Figure 22:
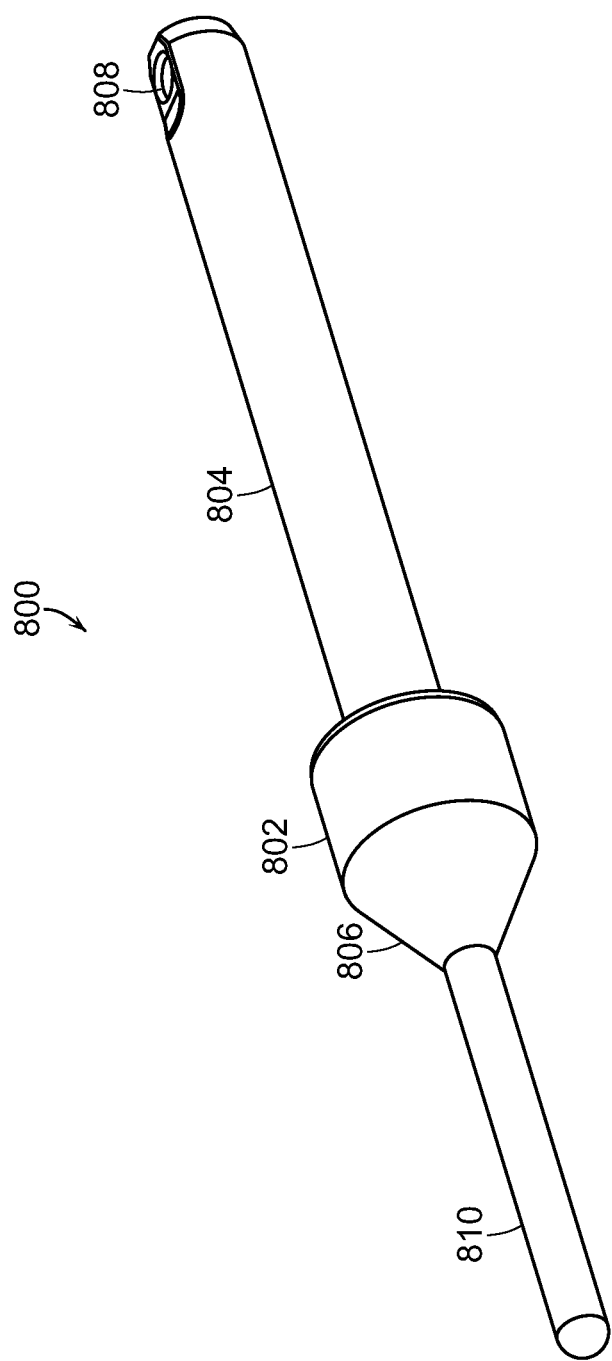
FIG. 22 is an exemplary embodiment of a push-in needle according to the present disclosure.

Turning now to FIG. 22, an exemplary needle 800 is illustrated for a push-in solenoid valve 60, including a needle head 802, a needle stem 804 and a needle tip 810. The diameter of the needle head 802 is greater than the diameter of the needle tip 810 to ensure a durable and/or tight seal can be created between the needle head 802 and the seat 700 when the needle tip 810 is pushed into the bore 702. The diameter of the needle tip 810 can be configured and dimensioned to pass unimpeded through the bore 702. In particular, the diameter of the needle tip 810 can be slightly smaller than the diameter of the bore 702 to permit the needle tip 810 to pass through the bore 702, while supporting the needle 800. Thus, no matter which dimensions and/or configurations of the needle 800 and/or seat 700 are being implemented, the diameter of the needle tip 810 will always be slightly smaller than the diameter of the bore 702. Although illustrated with a rounded needle tip 810 end, it should be understood that alternative configurations of the needle tip 810 end can be implemented, e.g., a pointed end, or the like.

The needle 800 includes an angular sealing surface 806 between the needle head 802 and the needle tip 810. In particular, the angular sealing surface 806 can act as a transition and/or connection area between the needle head 802 and the needle tip 810. The angular sealing surface 806 can be, e.g., sloping, convex, concave, or the like. Thus, when the needle tip 810 is pushed and/or translated into the bore 702 of the seat 700 to stop flow through the bore 702, the seat 700 can act as, e.g., a bushing, and the angular sealing surface 806 can self-center, e.g., align, guide, or the like, the needle 800 to ensure the needle head 802 is centered with respect to the bore 702. The needle head 802 and the needle stem 804 can include, e.g., an angled, perpendicular, or the like, transition and/or connection area therebetween. The needle 800 can further include an exterior coating of, e.g., gold, platinum, ceramic, polymer, and the like. The exterior coating can protect the needle 800 from, e.g., corrosion, pitting, and the like, caused by the system pressure loads and/or solvents involved during operation. Alternatively, rather than the entire needle 800 including the exterior coating, only the needle head 802 and/or the angular sealing surface 806 can include the exterior coating.

When the needle 800 is pushed into the bore 702 of the seat 700, a durable and/or tight seal is created between the angular sealing surface 806 and the bore edge 706. Upon initial contact of the angular sealing surface 806 and the bore edge 706, a plastic deformation of the bore edge 706 may occur. In particular, the plastic deformation can conform the bore edge 706 geometry to a complimentary angular sealing surface 806 geometry. For example, if the bore edge 706 is defined by a pointed junction between the outer side surface 710 and the bore 702, the bore edge 706 can plastically deform to a, e.g., sloping, convex, concave, or the like, surface complimentary to the angular sealing surface 806. The plastic deformation, in general, occurs during the first mating between the angular sealing surface 806 and the seat 700. However, it should be understood that the plastic deformation may occur after the first mating between the angular sealing surface 806 and the seat 700. The material of fabrication, e.g., the modulus of elasticity of the material of fabrication, for the seat 700 can be selected such that a plastic deformation only occurs at the bore edge 706 and does not continue to plastically deform during the lifetime of the seat 700. Upon the initial plastic deformation, the bore edge 706 surface complimentary to the angular sealing surface 806 ensures an enhanced seal between said elements. Thus, rather than a seal at a pointed junction between the bore edge 706 and the angular sealing surface 806, the larger contact and/or sealing surface area, i.e., the plastically deformed bore edge 706, reduces the chance of leakage through the seal.

Still with reference to FIG. 22, the exemplary needle 800 can include a needle bore 808 (or a keeper groove 208 of the needle 200) at a distal end of the needle stem 804. The needle bore 808 can be configured and dimensioned to mate with, e.g., a collar, bushing, washer, or the like, to securely attach the distal end of the needle stem 804 to a stem return spring mechanism. Although not illustrated, other embodiments of the exemplary needle 800 can include needle tip 810 and/or needle stem 804 grooves similar to those discussed with respect to needle 200. In particular, the needle tip 810 and/or needle stem 804 grooves can enhance the flow of the solvent 24 (e.g., mobile phase media 23) through the seat 700 by, e.g., reducing the flow resistance, increasing the flow path through the bore 702, or the like.

Figure 23A:
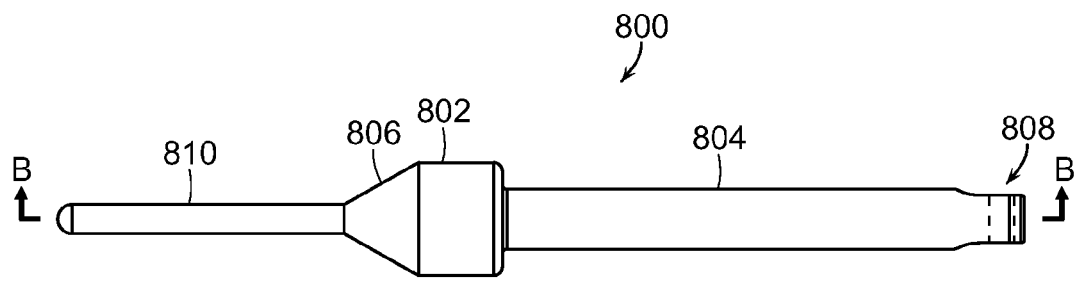
FIGS. 23A-D are side, cross-sectional and detailed views of an exemplary embodiment of a push-in needle according to the present disclosure.
Figure 23B:
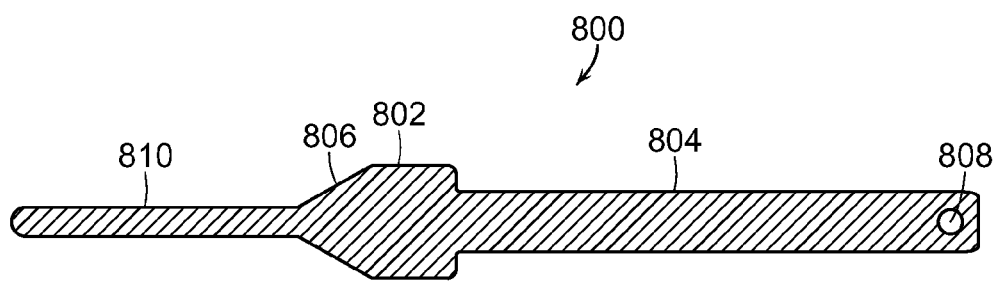
Figure 23C:
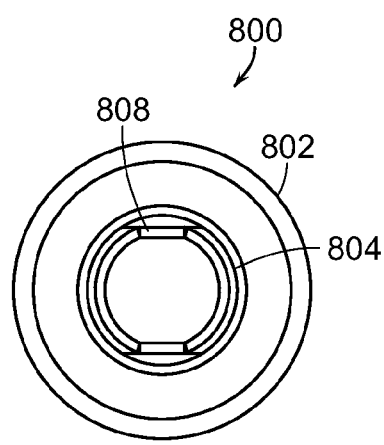
Figure 23D:
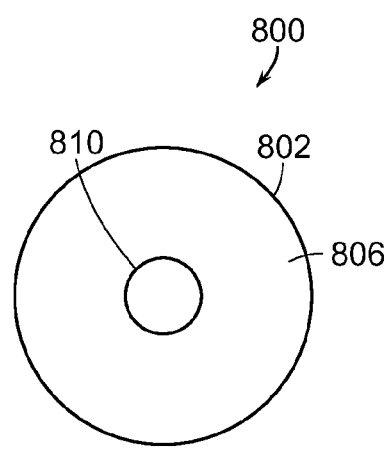

With respect to FIGS. 23A-D, cross-sectional, side and detailed views are provided of the exemplary needle 800. FIG. 23A illustrates a side view of the needle tip 810 and the needle head 802, including the angular sealing surface 806. In addition, FIG. 23A provides plane "B" for reference of the cross-sectional view of FIG. 23B. FIG. 23C is a back view of the needle 800. In particular, the relationship between the needle head 802 diameter and the needle stem 804 diameter can be seen, i.e., the needle head 802 diameter is greater than the needle stem 804 diameter. In addition, the needle bore 808 can be seen in the needle stem 804. The distal end of the needle stem 804 having the needle bore 808 passing therethrough may be, e.g., flattened, rather than maintaining the diameter of the needle stem 804. With reference to FIG. 23D, a front view of the needle head 802 is provided. In particular, the relationship between the needle head 802 diameter and the needle tip 810 diameter can be seen, i.e., the needle head 802 diameter is greater than the needle tip 810 diameter. It should be understood that once the push-in configuration of solenoid valve 60 is actuated into a closed position, i.e., the needle tip 810 has been pushed into the bore 802 and the angular sealing surface 806 has been pushed against the seat 700, the solvent (e.g., mobile phase media 23) cannot pass through the contact and/or sealing area of the angular sealing surface 806 and the bore edge 706.

Figure 24A:
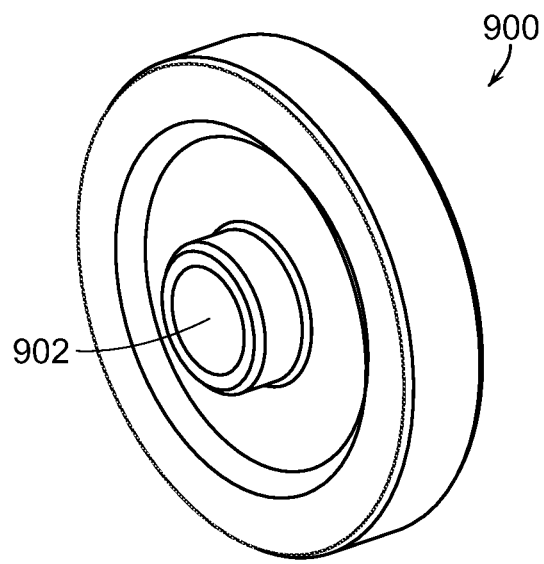
FIGS. 24A and 24B are exemplary embodiments of a stem seal according to the present disclosure.
Figure 24B:
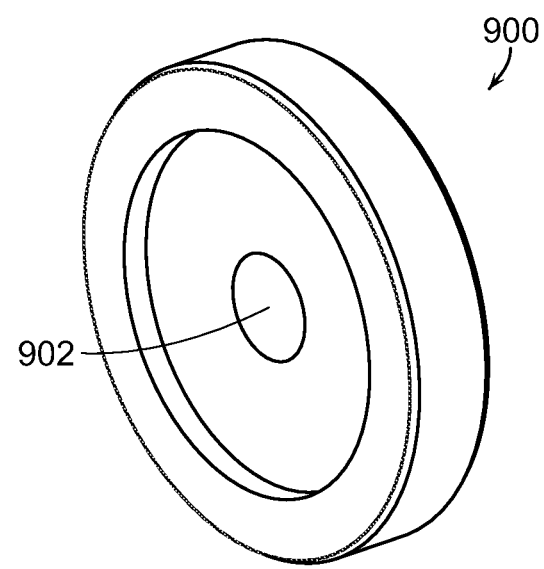
Figure 25A:
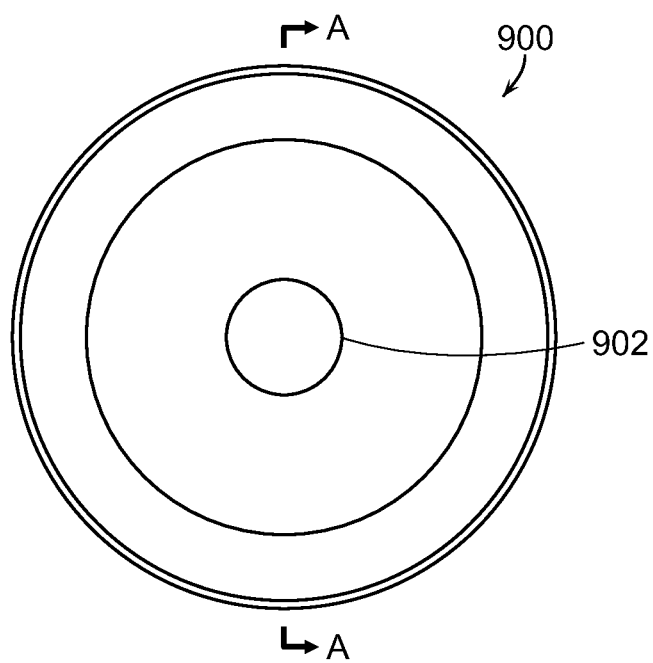
FIGS. 25A and 25B are front and cross-sectional views of an exemplary embodiment of a stem seal according to the present disclosure.
Figure 25B:
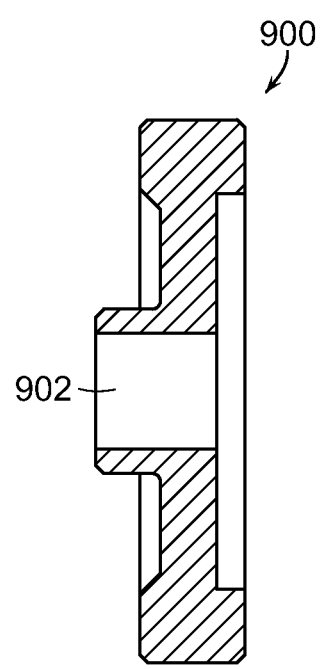

With reference to FIGS. 24A and 24B, an exemplary stem seal 900 is provided. The stem seal 900 is substantially similar to the stem seal 408 previously discussed with respect to the pull-through solenoid valve 60 configuration. The stem seal 900, e.g., an ACQUITY BSM seal, is secured within the head section 70 and creates a waterproof and/or pressure resistant seal between the stem return spring mechanism 402 and/or the actuator section 72, e.g., to prevent leakage of the solvent 24 (e.g., mobile phase media 23) through the stem seal bore 902 in which the needle stem 804 is situated (see, e.g., Waters Technologies Corporation, Massachusetts, USA, Head Plunger Seal, Product Number 700002599 (2011)). The stem seal 900 can be disposed around the needle stem 804 and between the stem return spring plate 410 and the valve body 64. The needle stem 804 is configured and dimensioned to permit translation of the needle stem 804 through the seal bore 902. Further, the stem seal 900 ensures that the solvent 24 (e.g., mobile phase media 23) flowing into the cavity 406 of the head section 70 creates a pressure sufficient to vent and/or flow the solvent 24 (e.g., mobile phase media 23) out of the solenoid valve 70 through the outlet port 68. The stem seal bore 902 can be dimensioned to receive the pull-through needle 200 and/or the push-in needle 800. FIGS. 25A and 25B illustrate a front and a cross-sectional view of the exemplary stem seal 900. In particular, FIG. 25A provides plane "A" for reference of the cross-sectional view of FIG. 25B.

Figure 26A:
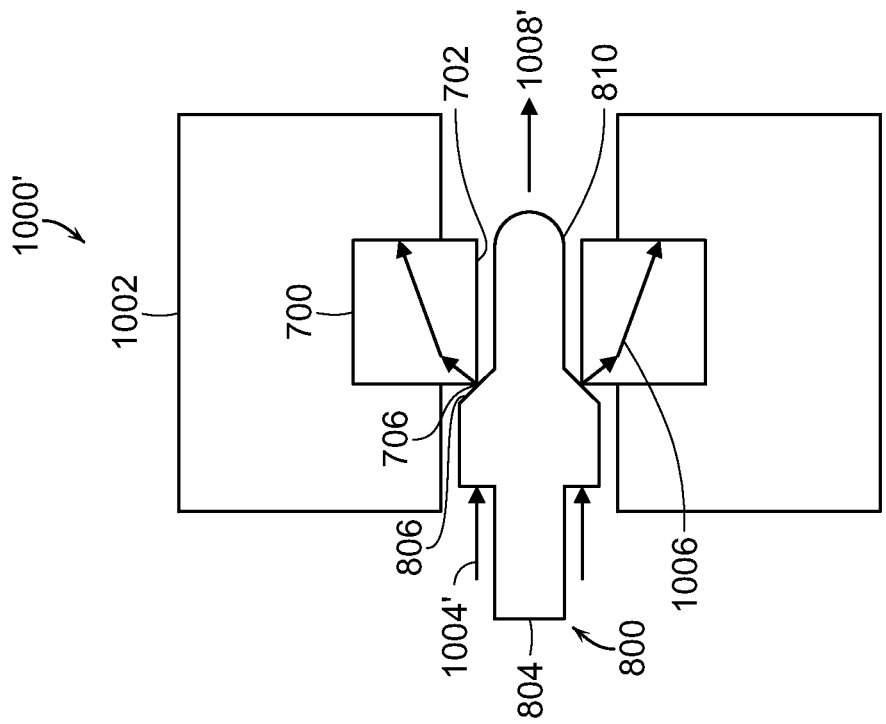
FIGS. 26A and 26B are exemplary embodiments of a seat retainer assembly illustrating a pressure assist according to the present disclosure.
Figure 26B:
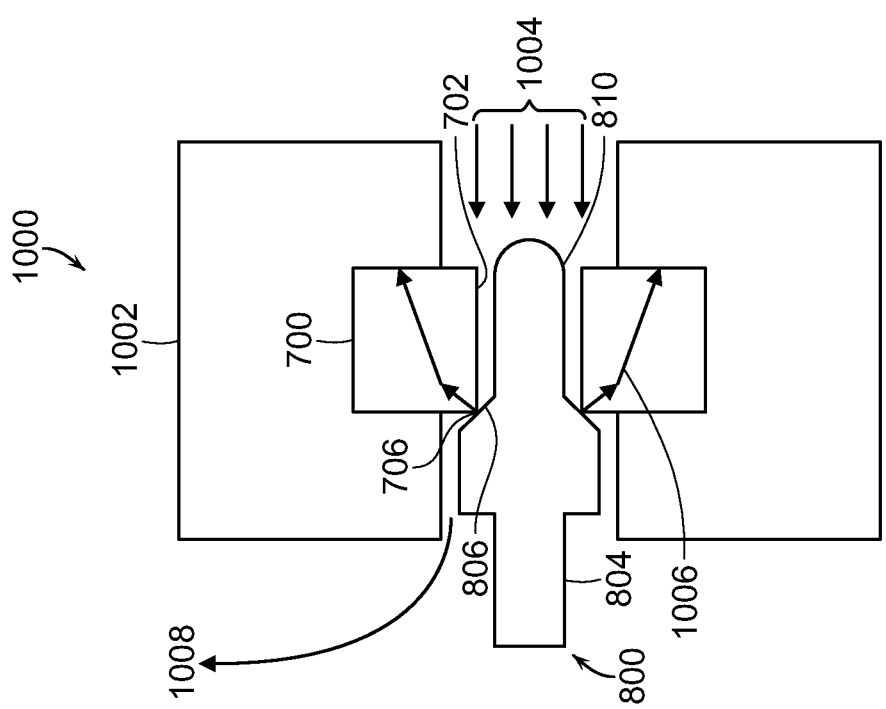

Turning now to FIGS. 26A and 26B, seat retainer assemblies 1000 and 1000' are depicted, including a seat retainer 1002, a seat 700 and a needle 800. The seat retainer assemblies 1000 and 1000' are substantially similar to the seat retainer assemblies 300 and 300' of FIGS. 13A and 13B, except the solenoid valve 60 configuration being depicted is a push-in needle 800 solenoid valve 60. The seat retainer 1002 can be securely disposed inside the head section 70 of FIG. 6. The seat 700 can be securely disposed inside the seat retainer 1002. As described previously, although not illustrated in FIGS. 26A and 26B, the seat groove 408 can mate with protrusions, e.g., ridges, spikes, or the like, of the internal contact surface of the seat retainer 1002 to prevent undesired movement of the seat 700 in the seat retainer 1002. The needle tip 810 is at least partially disposed inside the bore 702 of the seat 700 and can be pushed into the bore 702 until the angular sealing surface 806 creates a seal against the bore edge 706. The needle bore 808 at the distal end of the needle stem 804 can be secured to a stem return spring mechanism (not shown).

With respect to FIG. 26A, flow of the solvent (e.g., mobile phase media 23) can enter the seat retainer assembly 1000 through the inlet port 66 and can proceed in the direction illustrated by inlet arrows 1004. Although illustrated in a closed position, i.e., the angular sealing surface 806 is pressed against the bore edge 706, it should be understood that in an open position, an open flow path between the bore edge 706 and the angular sealing surface 806 is available for the solvent 24 (e.g., mobile phase media 23) to pass through unimpeded. The open flow path, i.e., an annular gap, can be in the range of, e.g., about 0.005 to 0.010 inches. Thus, the solvent 24 (e.g., mobile phase media 23) can enter through the inlet port 66, flow through the bore 702 and over the needle tip 810, flow over the angular sealing surface 806 and the needle head 802, and can further vent and/or flow out of the outlet port 68 in the direction shown by the outlet arrow 1008.

The exemplary push-in needle 800 configuration of FIG. 26A further permits the use of a pressure assist from the system pressure to actuate the solenoid valve 60 into an open position, i.e., create a flow path opening between the angular sealing surface 806 and the bore edge 706 and/or the seat 700. In particular, to actuate the solenoid valve 60 into a closed position, the needle tip 810 can be pushed into the bore 702 in an upstream direction to press the angular sealing surface 806 against the bore edge 706 and/or the seat 700. As would be understood by those of skill in the art, the flow of the solvent 24 (e.g., mobile phase media 23) from the inlet port 66 enters the seat retainer assembly 1000 as indicated by the inlet arrows 1004. Thus, the solvent 24 (e.g., mobile phase media 23) creates a pressure force due to the pressure of the system 10 on the angular sealing surface 806 in the direction of the outlet arrow 1008. The opening and closing forces necessary for opening and closing the solenoid valve 60 can be represented by Equations 3 and 4 below.

$$OA = A_1 \times P \tag{3}$$

$$CF = A_2 \times P \tag{4}$$

wherein OA is the opening force, CF is the closing force, $A_1$ is the shaft seal area, i.e., the seal area between the stem seal 900 and the needle stem 804, $A_2$ is the needle tip 810/seat 700 seal area, i.e., the area between the needle tip 810 and the bore 702 of the seat 700, and P is the system pressure on the angular sealing surface 806.

The pressure force on the angular sealing surface 806 assist in translating the needle tip 810 and the needle head 802 out of the bore 702 to create a flow path opening between the angular sealing surface 806 and the bore edge 706. The added pressure force on the angular sealing surface 806 of the exemplary seat retainer assembly 1000 enhances the ability and/or timing for the solenoid valve 60 to actuate into an open position. As illustrated by the load path arrows 1006 in FIG. 26A, the sealing force created by pushing the needle 800 into the seat 700 and against the bore edge 706 creates a pressure load which passes through the seat 700 and is further transmitted into the seat retainer 1002, which absorbs the pressure forces, thereby providing support for the seat 700 and the needle 800 and/or prevents transmission of the pressure forces to other components of the assembly.

It should be understood that, e.g., the diameter of the sealing surface, the diameter of the bore 702, the diameter of the bore edge 706, the diameter of the needle tip 810, the surface area of the angular sealing surface 806, and the like, can be configured and dimensioned to modify the pressure assist created by the system pressure. For example, the surface area of the angular sealing surface 806 inside the bore 702 can be increased to create a larger surface area upon which the pressure forces act, thereby increasing the pressure assist for opening the seal between the angular sealing surface 806 and the bore edge 706.

With respect to FIG. 26B, flow of the solvent 24 (e.g., mobile phase media 23) can enter the seat retainer assembly 1000' through the outlet port 68 and can proceed in the direction illustrated by the inlet arrows 1004'. Although illustrated in a closed position, i.e., the angular sealing surface 806 is pressed against the bore edge 706, it should be understood that in an open position, an open flow path between the bore edge 706 and the angular sealing surface 806 is available for the solvent 24 (e.g., mobile phase media 23) to pass through unimpeded. Thus, the solvent 24 (e.g., mobile phase media 23) can enter through the outlet port 68, flow over the needle head 802 and the angular sealing surface 806, flow through the bore 702 and further vent and/or flow out of the inlet port 66 in the direction shown by the outlet arrow 1008'.

The exemplary push-in needle 800 configuration of FIG. 26B further permits the use of a pressure assist from the system pressure to seal the angular sealing surface 806 against the bore edge 706 and/or the seat 700. In particular, to actuate the solenoid valve 60 into a closed position, the needle tip 810 and the needle head 802 can be pushed in a downstream direction into the bore 702 to press the angular sealing surface 806 against the bore edge 706 and/or the seat 700. As would be understood by those of skill in the art, the flow of the solvent 24 (e.g., mobile phase media 23) from the outlet port 68 enters the seat retainer assembly 1000' as indicated by the inlet arrows 1004'. Thus, the solvent 24 (e.g., mobile phase media 23) creates a pressure force due to the pressure of the system 10 on a back surface of the needle head 802 against the seat 700. In particular, the back surface of the needle head 802 on which the pressure force is provided by the system 10 is the net pressure area, as it is the area of the pressure not countered by pressure elsewhere on the needle 800. The pressure force can be represented by Equation 5, below:

$$F = P \times (A_{seat} - A_{shaft}) \quad (5)$$

wherein F is the pressure force, P is the system pressure, $A_{seat}$ is the exposed area of the seat 700, and $A_{shaft}$ is the area of the needle tip 810.

The pressure force on the back surface of the needle head 802 against the seat 700 assists in pushing the needle tip 810 into the bore 702 and further assists in pressing and/or sealing the angular sealing surface 806 against the bore edge 706. The added pressure force on the needle head 802 is thereby supported through the sealing surface, i.e., the contact area between the bore edge 706 and the angular sealing surface 806, to enhance the seal and/or improve the sealing stress between said components.

As illustrated by the load path arrows 1006, the sealing force created by pushing the needle 800 into the seat 700 in conjunction with the pressure assist force creates a pressure load which passes through the needle seat 100 and is further transmitted into the seat retainer 1002, which absorbs the pressure forces, thereby providing support for the seat 700 and the needle 800 and/or prevents transmission of the pressure forces to other components of the assembly.

Similar to the seat retainer assembly 1000, it should be understood that, e.g., the diameter of the sealing surface, the diameter of the bore 702, the diameter of the bore edge 706, the diameter of the needle tip 810, the surface area of the angular sealing surface 806, and the like, can be configured and dimensioned to modify the pressure assist created by the system pressure. For example, the surface area of the back surface of the needle head 802 can be increased to create a larger surface area upon which the pressure forces act, thereby increasing the pressure assist and/or sealing the angular sealing surface 806 against the bore edge 706. The materials of fabrication of the needle 800 and the seat 700 can further be selected to prevent damage of said components when a pressure assist force is introduced against the needle head 802.

Figure 27:
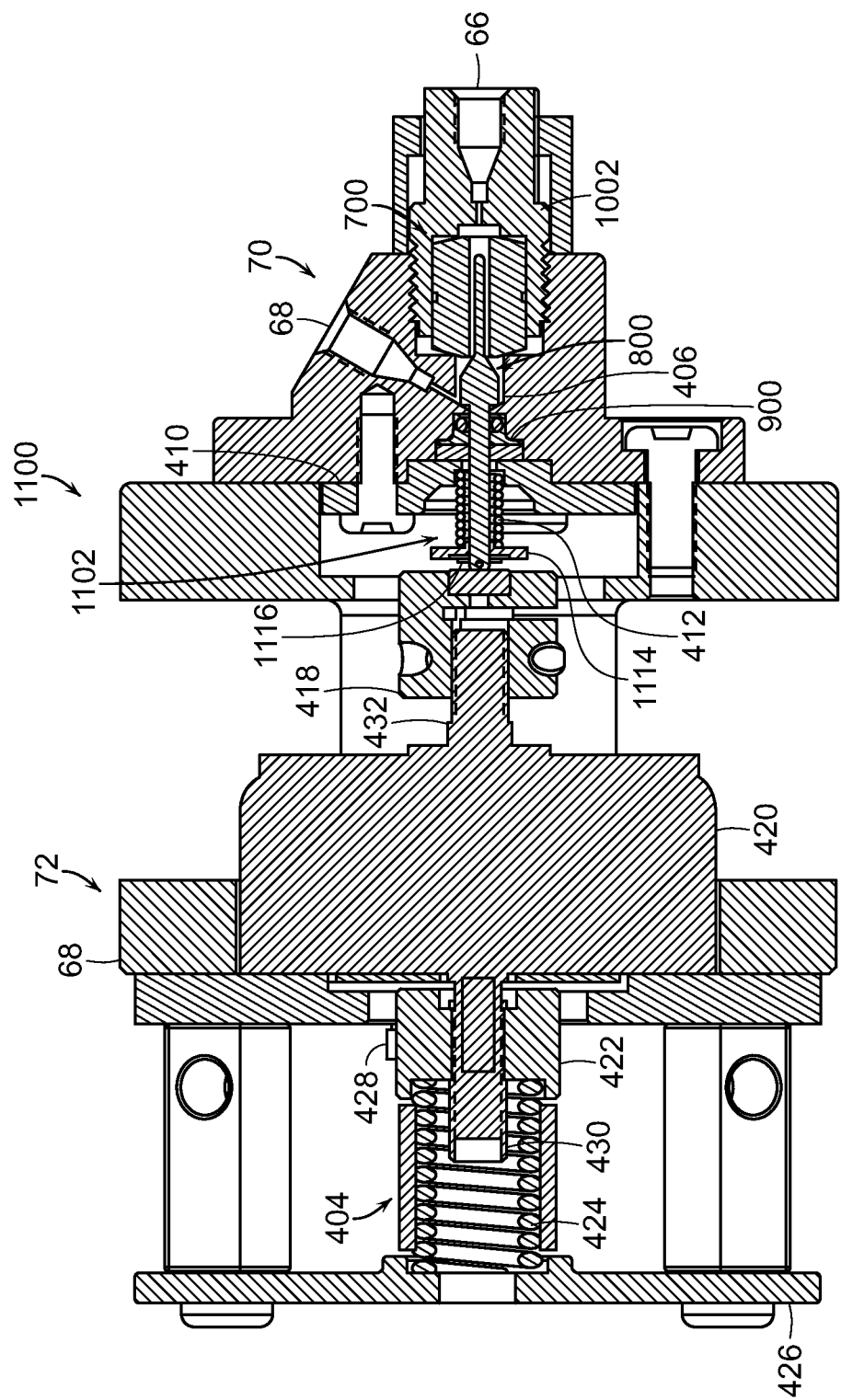
FIG. 27 is an exemplary embodiment of a push-in solenoid valve in an open position according to the present disclosure.

Turning now to FIG. 27, an exemplary embodiment of a push-in solenoid valve 1100 is depicted in an open position, i.e., a flow path exists between the angular sealing surface 806 of the needle 800 and the bore edge 706 of the seat 700. The solenoid valve 1100 is substantially similar to the solenoid valve 400 previously discussed with respect to the pull-through configuration. However, rather than implementing the pull-through configuration components, the push-in configuration solenoid valve 1100 implements, e.g., a push-in seat 700, a push-in needle 800, and actuates the stem return spring 412 and the solenoid return spring 424 such that the needle 800 is pushed into the seat 700 to stop flow through the bore 702. It should be understood that the exemplary modular solenoid valve 60 kit allows a user to implement components identical for both the push-in and the pull-through configuration to create both configurations, while interchanging the components which differ in each configuration, e.g., the needle, seat, and the like, to specifically create either a pull-through or a push-in solenoid valve 60. Thus, less replacement components (e.g., less replacement stock) are needed to create the desired solenoid valve 60 configurations. In particular, the solenoid valve 1100 includes a valve body 64, which includes an actuator section 72 and a head section 70. The seat retainer assembly 1000 is securely disposed inside the head section 70, including the seat retainer 1002, the seat 700 and the needle 800. The head section 70 further includes the inlet port 66 and the outlet port 68.

A stem return spring mechanism 1102 disposed inside the valve body 64 includes, e.g., a stem return spring 412, a collar 1114, and a locking pin 1116. The stem return spring mechanism 1102 is securely connected to a distal end of the needle stem 804 with respect to the needle tip 810. The collar 1114 has an inner bore dimensioned to fit around the needle stem 804. In particular, the collar 1114 can be fastened to the needle stem 804 with the locking pin 1116, which is configured and dimensioned to mate with the needle bore 808 of the needle stem 804. The stem return spring mechanism 1102 is thereby designed to move and/or translate the needle 800 to actuate the solenoid valve 1100 into an open or closed position. The stem return spring 412 can be disposed around the needle stem 804 and can provide pressure directly against the collar 1114 and a stem return spring plate 410. The stem return spring plate 410 is securely fastened to the valve body 64. The needle stem 804 further translates through a bore in the stem return spring plate 410.

The stem return spring 412 can be compressed by applying a compression force on the distal end of the needle stem 804 and, thereby, the collar 1114, in the direction of the stem return spring plate 410. The motion of compressing the stem return spring 412 actuates the solenoid valve 1100 into a closed position. In particular, as the stem return spring 412 is compressed, the needle head 802 and the needle tip 810 are sufficiently pushed into the seat 700 to provide a sealing stress between the angular sealing surface 806 and the bore edge 706, i.e., sealing the flow path opening between the angular sealing surface 806 and the bore edge 706. As should be understood by those of skill in the art, when the stem return spring 412 is in a compressed state between the stem return spring plate 410 and the collar 1114, the mechanical energy stored in the stem return spring 412 provides an expansion force against said components to expand the stem return spring 412 to its natural length. When the stem return spring 412 expands, the force against the collar 1114 and the stem return spring plate 410 translates the needle tip 810 out of the bore 702 in a direction away from the stem return spring plate 410. The solenoid valve 1100 is thereby actuated into an open position, i.e., a flow path opening is created between the angular sealing surface 806 and the bore edge 706. Based on the upstream and downstream configuration of the solenoid valve 60, the pressure assist previously discussed either enhances the sealing stress, i.e., the sealing force, on the seal or enhances the ability of the solenoid valve 1100 to actuate into an open position.

On a side opposing the stem return spring 412, the stem return spring plate 410 can include a stem seal 900, e.g., an ACQUITY BSM seal, securely disposed around the needle stem 804 and between the stem return spring plate 410 and the valve body 64 (see, e.g., Waters Technologies Corporation, Massachusetts, USA, Head Plunger Seal, Product Number 700002599 (2011)). The stem seal 900 can ensure a waterproof and/or pressure resistant seal between the head section 70 and the return spring mechanism 402 and/or the actuator section 72, e.g., to prevent leakage of the solvent 24 (e.g., mobile phase media 23) through the bore in which the needle stem 804 is situated. Further, the head section 70 includes a cavity 406 into which the solvent 24 (e.g., mobile phase media 23) flows after passing through the bore 702. The stem seal 900 ensures that the solvent 24 (e.g., mobile phase media 23) flowing into the cavity 406 creates a pressure sufficient to vent and/or force the solvent 24 (e.g., mobile phase media 23) out of the solenoid valve 1100 through the outlet port 68.

Still with reference to FIG. 27, the actuator section 72 includes the solenoid return spring mechanism which further includes a solenoid return spring 424, a solenoid stroke calibration collar 422, a stem/solenoid calibration collar 418 (i.e., an actuator-to-head calibration collar) and an actuator 420 (i.e., a drive solenoid). In particular, the solenoid stroke calibration collar 422 is securely fastened to a rear shaft 430 of the actuator 420. The solenoid stroke calibration collar 422 and the rear shaft 430 can be, e.g., threaded, or the like, to permit a calibration and/or adjustment of the position of the solenoid stroke calibration collar 422 along the rear shaft 430. The solenoid stroke calibration collar 422 can further include a clamping feature for enhanced adjustment along and/or attachment to the rear shaft 430. Thus, the compression and/or expansion forces produced by the solenoid return spring 424 can be adjusted for a desired system pressure being implemented. The solenoid return spring 424 is disposed around the rear shaft 430 and between the solenoid stroke calibration collar 422 and a solenoid return spring plate 426. Further, the solenoid return spring 424 can be securely attached to the solenoid stroke calibration collar 422 and/or the solenoid return spring plate 426. Thus, the solenoid return spring 424 can be compressed and/or expanded between the solenoid return spring plate 426 and the solenoid stroke calibration collar 422. As would be understood by those of skill in the art, a compression and/or expansion of the solenoid return spring 424 transmits the compression and/or expansion force to the solenoid stroke calibration collar 422, which in turn translates the actuator 420 towards and/or away from the solenoid return spring plate 426. An actuator guide protrusion 428 can pass through a bore of the valve body 64 and can assist in guiding the actuator 420 along an even and/or straight path. Although illustrated with one actuator guide protrusion 428, it should be understood that a greater and/or lesser number of actuator guide protrusions 428 can be implemented, e.g., zero, one, two, three, four, or the like.

A collar protrusion 432 extending from an actuator 420 side opposing the solenoid return spring 424 is utilized for attachment of the stem/solenoid calibration collar 418. The collar protrusion 432 and the stem/solenoid calibration collar 418 can be, e.g., threaded, or the like, to permit a calibration and/or adjustment of the position of the stem/solenoid calibration collar 418 along the collar protrusion 432. The stem/solenoid calibration collar 418 can further include a clamping feature for enhanced adjustment along and/or attachment to the collar protrusion 432. Thus, the distance of translation of the stem/solenoid calibration collar 418 can be adjusted for a desired system pressure being implemented. The stem/solenoid calibration collar 418 is in communication with the stem return spring mechanism 402. In particular, the stem/solenoid calibration collar 418 can, e.g., provide and/or remove a force against the distal end of the needle stem 804 to translate the needle tip 810 and the angular sealing surface 806 into the bore 702 to actuate the solenoid valve 1100 into one of a closed and an open position, respectively.

Figure 28:
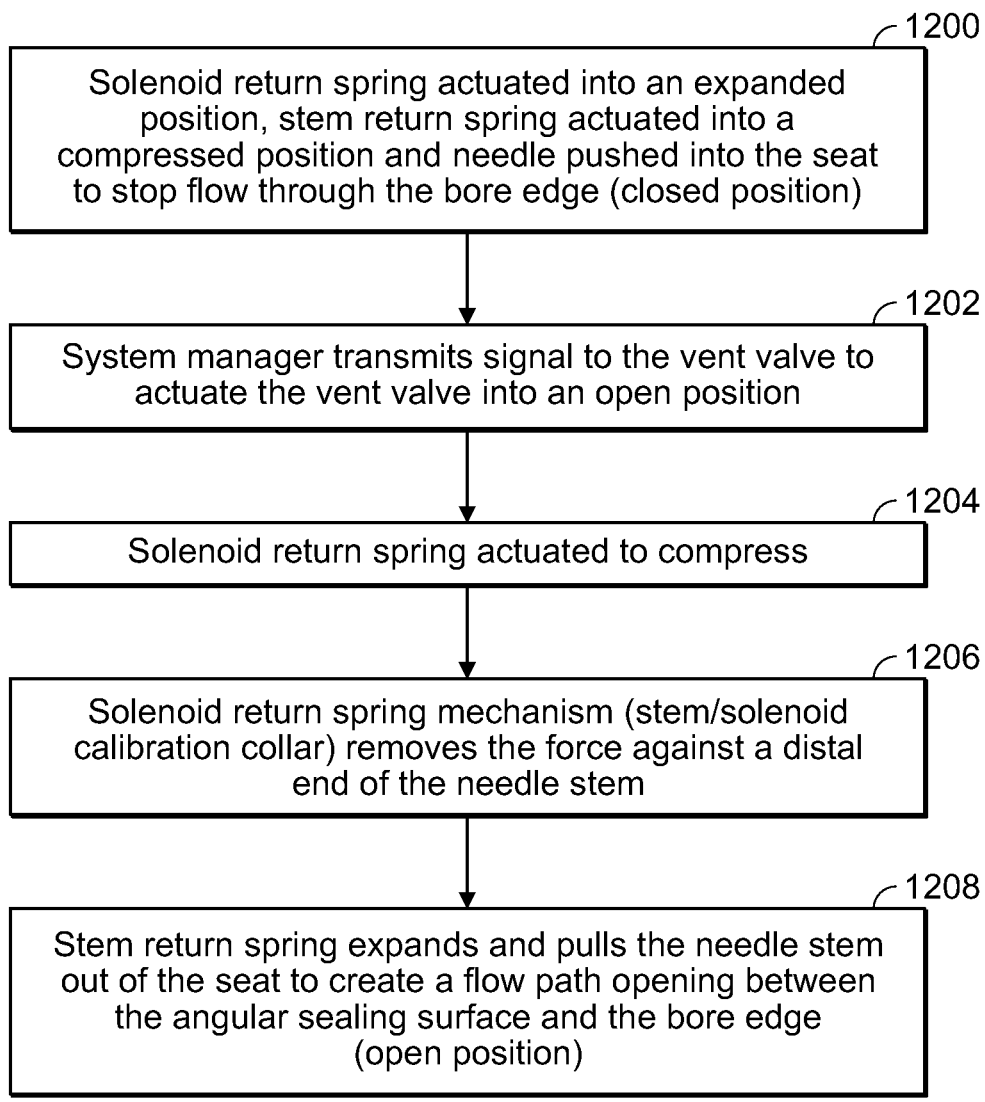
FIG. 28 is a block diagram for actuating an exemplary embodiment of a push-in normally closed solenoid valve into an open position according to the present disclosure.

The exemplary solenoid valve 1100 can be configured as one of a push-in normally closed valve or a push-in normally open valve. With respect to the push-in normally closed valve and the block diagram of FIG. 28, the spring constants for the stem return spring 412 and the solenoid return spring 424 can be adjusted and/or selected according to the operational pressure to ensure that the stem return spring 412 is normally compressed and the solenoid return spring 424 is normally actuated into an expanded position (1200). As discussed previously, the expanded setting of the solenoid return spring 424 translates the actuator 420 and the stem/solenoid calibration collar 418 in the direction of the stem return spring mechanism 1116. Thus, the stem/solenoid calibration collar 418 provides a force against the distal end of the needle stem 804 when the solenoid return spring 424 is expanded, causing the stem return spring 412 to compress. In particular, the spring constant of the solenoid return spring 424 can be selected such that it overcomes the spring constant of the stem return spring 412. The compressed setting of the stem return spring 412, in conjunction with the force on the distal end of the needle stem 204, provides a pulling force on the collar 1114, which in turn translates the needle tip 810 and angular sealing surface 806 into the bore 702 to actuate the solenoid valve 1100 into a closed position, i.e., the angular sealing surface 806 of the needle 800 is pushed tightly against the bore edge 706 of the seat 700 to stop flow through the bore 702 (1200). The system/convergence manager 20, discussed previously, is in communication with the solenoid valve 60 and can transmit a signal to the solenoid valve 1100 to compress the solenoid return spring 424 to actuate the solenoid valve 60 into an open position (1202). As would be understood by those of skill in the art, when the solenoid return spring 424 is actuated to compress (1204), the force on the distal end of the needle stem 804 by the stem/solenoid calibration collar 418 is removed (1206). The spring constant of the stem return spring 412 can be selected such that when the force generated against the distal end of the needle stem 804 is removed, the stem return spring 412 can automatically expand to open the solenoid valve 1100. Thus, as the solenoid return spring 424 compresses, the stem return spring 412 expands and translates the collar 1114 in a direction away from the stem return spring plate 410, thereby pulling the needle tip 810 and the angular sealing surface 806 out of the bore 702 of the seat 700 to create an opening between the angular sealing surface 806 and the bore edge 706, i.e., the solenoid valve 1100 is actuated into an open position (1208).

Figure 29:
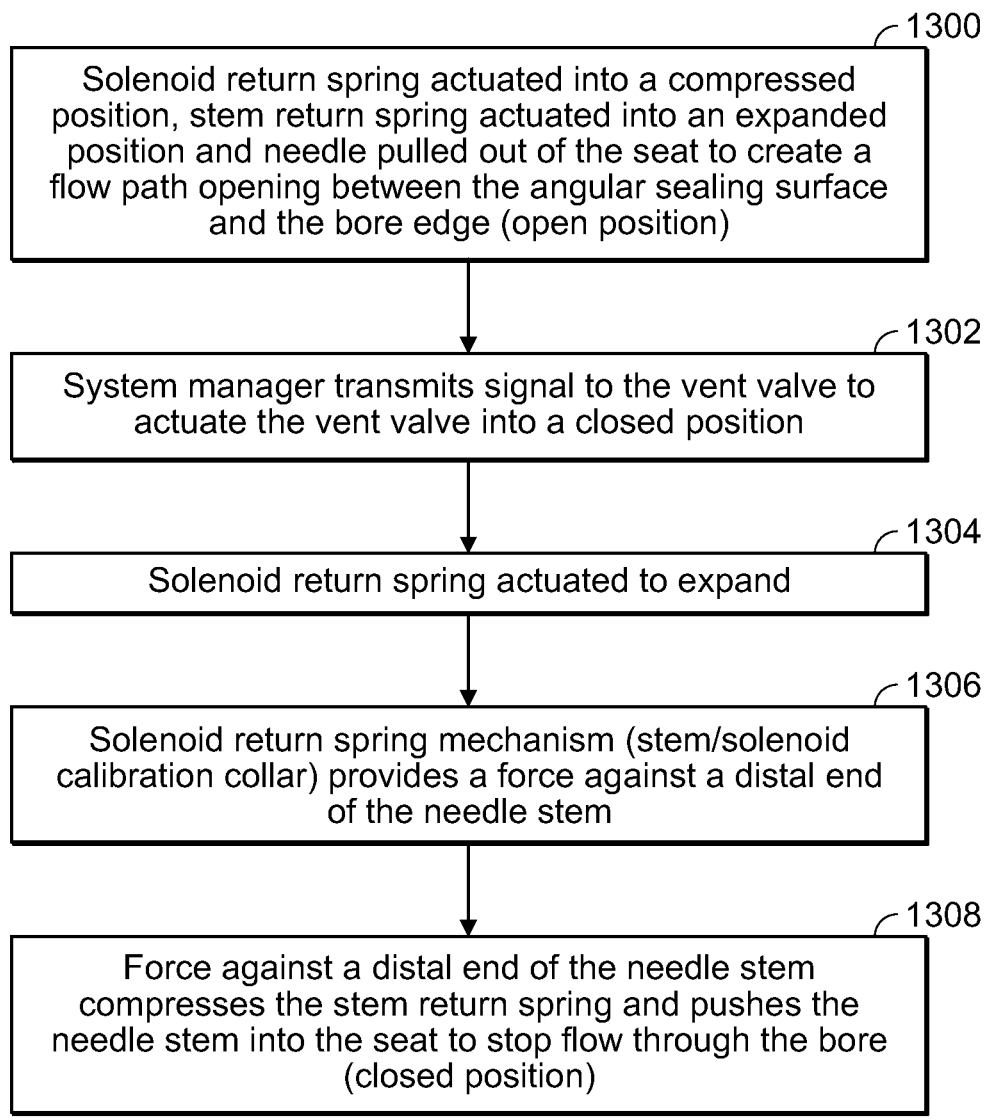
FIG. 29 is a block diagram for actuating an exemplary embodiment of a push-in normally open solenoid valve into a closed position according to the present disclosure.

With respect to the push-in normally open valve and the block diagram of FIG. 29, the spring constants for the stem return spring 412 and the solenoid return spring 424 can be adjusted and/or selected according to the operational pressure to ensure that the stem return spring 412 is normally expanded and the solenoid return spring 424 is normally actuated into a compressed position (1300). As discussed previously, the expanded setting of the stem return spring 412 provides an expansion force against the stem return spring plate 410, which in turn pulls the needle tip 810 and the angular sealing surface 806 out of the seat 100, i.e., a flow opening exists between the angular sealing surface 806 and the bore edge 706 to permit flow through the bore 702 (1300). The compressed setting of the solenoid return spring 424 translates and/or retracts the actuator 420 and the stem/solenoid calibration collar 418 in a direction away from the stem return spring mechanism 1016. Thus, the stem/solenoid calibration collar 418 does not provide a force against the distal end of the needle stem 804 when the solenoid return spring 414 is compressed. The system/convergence manager 20, discussed previously, is in communication with the solenoid valve 1100 and can transmit a signal to the solenoid valve 1100 to expand the solenoid return spring 424 to actuate the solenoid valve 1100 into a closed position (1302). As would be understood by those of skill in the art, when the solenoid return spring 424 is actuated to expand (1304), the expansion force generates a force by the stem/solenoid calibration collar 418 against the distal end of the needle stem 804 (1306). The spring constant of the solenoid return spring 424 can be selected such that the force generated against the distal end of the needle stem 804 is sufficient to overcome the expansion force of the stem return spring 412. Thus, as the solenoid return spring 424 expands, the stem return spring 412 is compressed and the needle tip 810 and the angular sealing surface 806 are pushed against and/or into the bore 702 of the seat 700, i.e., the solenoid valve 1100 is actuated into a closed position (1308).

As discussed previously and now illustrated in Table 2 below, a pressure assist from the system 10 can either enhance the sealing stress, i.e., the sealing force, on the seal or enhances the ability of the solenoid valve 1100 to actuate into an open position based on the upstream and downstream configuration of the push-in solenoid valve 1100. The "Solenoid Actuation" is the directional actuation of the solenoid return spring 424 to open or close the solenoid valve 1100, i.e., the solenoid return spring 424 compresses away from the seat 700 to open the solenoid valve 1100 and expands toward the seat 700 to close the solenoid valve 1100. The "Seat Port" indicates the port of entry of the solvent 24 (e.g., the mobile phase media 23) into the solenoid valve 1100, i.e., inlet indicating entry through the inlet port 66 and outlet indicating entry through the outlet port 68. The "Seal/Seal Diameters" is the relationship between the sealing diameter of the needle stem 804 and the seat seal 900, i.e., the seal diameter, and the sealing diameter of the angular sealing surface 806 to the bore edge 706, i.e., the seat diameter. The area associated with these diameters determines the pressure load on the needle 800. For example, for a push-in needle 800, the pressure load when closed is the pressure times the difference in area between the stem seal 900/needle stem 804 sealing area and the seat 700/angular sealing surface 806 sealing area. The "Normal Condition" indicates whether the solenoid valve 1100 is normally open or normally closed. The "Pressure Assist Action (closed)" and "Pressure Assist Action (open)" specify the direction of the pressure assist load due to pressure in the closed and open conditions, respectively. Thus, if the pressure assist is close for the "Pressure Assist Action (closed)", the pressure assist adds an additional force to closing the solenoid valve 1100. In contrast, if the pressure assist is open for the "Pressure Assist Action (closed)", the pressure assist adds an additional force to open the solenoid valve 1100.

TABLE 2

Push-In Modular Solenoid Valve Configurations and Resulting Behaviors

| | Configuration | | | | Behavior | |
|---|---|---|---|---|---|---|
| No. | Solenoid Actuation | Seat Port | Seat/Seal Diameters | Normal Condition | Pressure Assist Action (closed) | Pressure Assist Action (open) |
| 1 | Away from seat | Inlet | Any | Closed | Open | Open |
| 2 | Away from seat | Outlet | Seat > Seal | Closed | Close | Open |
| 3 | Away from seat | Outlet | Seat < Seal | Closed | Open | Open |
| 4 | Toward seat | Inlet | Any | Open | Open | Open |
| 5 | Toward seat | Outlet | Seat > Seal | Open | Close | Open |
| 6 | Toward seat | Outlet | Seat < Seal | Open | Open | Open |

In the first exemplary configuration, the solenoid valve 1100 is a push-in normally closed solenoid valve 1100 with the solvent 64 (e.g., mobile phase media 23) entering the solenoid valve 1100 through the inlet port 66. The solenoid return spring 424 actuates away from the seat 700 to open the solenoid valve 1100. The "seat diameter", i.e., the sealing diameter of the angular sealing surface 806 to the bore edge 706, can be either greater and/or lesser than the "seal diameter", i.e., the sealing diameter of the needle stem 804 and seat seal 900. The pressure assist created by the entry of the solvent 24 through the inlet port 66 provides a force on the angular sealing surface 806 and further assists in opening the solenoid valve 1100 in both the closed and open positions.

In the second exemplary configuration, the solenoid valve 1100 is a push-in normally closed solenoid valve 1100 with the solvent 24 entering the solenoid valve 1100 through the outlet port 68. The solenoid return spring 424 also actuates away from the seat 700 to open the solenoid valve 1100. The "seat diameter", i.e., the sealing diameter of the angular sealing surface 806 to the bore edge 706, is greater than the "seal diameter", i.e., the sealing diameter of the needle stem 804 and seat seal 900. The pressure assist created by entry of the solvent 24 through the outlet port 68 provides a force which assists in closing the solenoid valve 1100 in the closed position and opening the solenoid valve 1100 in an open position.

In the third exemplary configuration, the solenoid valve 1100 is a push-in normally closed solenoid valve 1100 with the solvent 24 entering the solenoid valve 1100 through the outlet port 68. The solenoid return spring 424 also actuates away from the seat 700 to open the solenoid valve 1100. The "seat diameter", i.e., the sealing diameter of the angular sealing surface 806 to the bore edge 706, is less than the "seal diameter", i.e., the sealing diameter of the needle stem 804 and seat seal 900. The pressure assist created by entry of the solvent 24 through the outlet port 68 provides a force which assists in opening the solenoid valve 1100 in both the open and closed positions.

In the fourth exemplary configuration, the solenoid valve 1100 is a push-in normally open solenoid valve 1100 with the solvent 24 entering the solenoid valve 1100 through the inlet port 66. The solenoid return spring 424 actuates toward the seat 700 to close the solenoid valve 1100. The "seat diameter", i.e., the sealing diameter of the angular sealing surface 806 to the bore edge 706, can be either greater and/or lesser than the "seal diameter", i.e., the sealing diameter of the needle stem 804 and seat seal 900. The pressure assist created by entry of the solvent 24 through the inlet port 66 provides a force which assists in opening the solenoid valve 1100 in both the open and closed positions.

In the fifth exemplary configuration, the solenoid valve 1100 is a push-in normally open solenoid valve 1100 with the solvent 24 entering the solenoid valve 1100 through the outlet port 68. The solenoid return spring 424 also actuates toward the seat 700 to close the solenoid valve 1100. The "seat diameter", i.e., the sealing diameter of the angular sealing surface 806 to the bore edge 706, is greater than the "seal diameter", i.e., the sealing diameter of the needle stem 804 and seat seal 900. The pressure assist created by entry of the solvent 24 through the outlet port 68 provides a force which assists in closing the solenoid valve 1100 in a closed position and opening the solenoid valve 1100 in an open position.

In the sixth exemplary configuration, the solenoid valve 1100 is a push-in normally open solenoid valve 1100 with the solvent 24 entering the solenoid valve 1100 through the outlet port 68. The solenoid return spring 424 also actuates toward the seat 700 to close the solenoid valve 1100. The "seat diameter", i.e., the sealing diameter of the angular sealing surface 806 to the bore edge 706, is less than the "seal diameter", i.e., the sealing diameter of the needle stem 804 and seat seal 900. The pressure assist created by entry of the solvent 24 through the outlet port 68 provides a force which assist in opening the solenoid valve 11 in both the closed and open positions.

Figure 30:
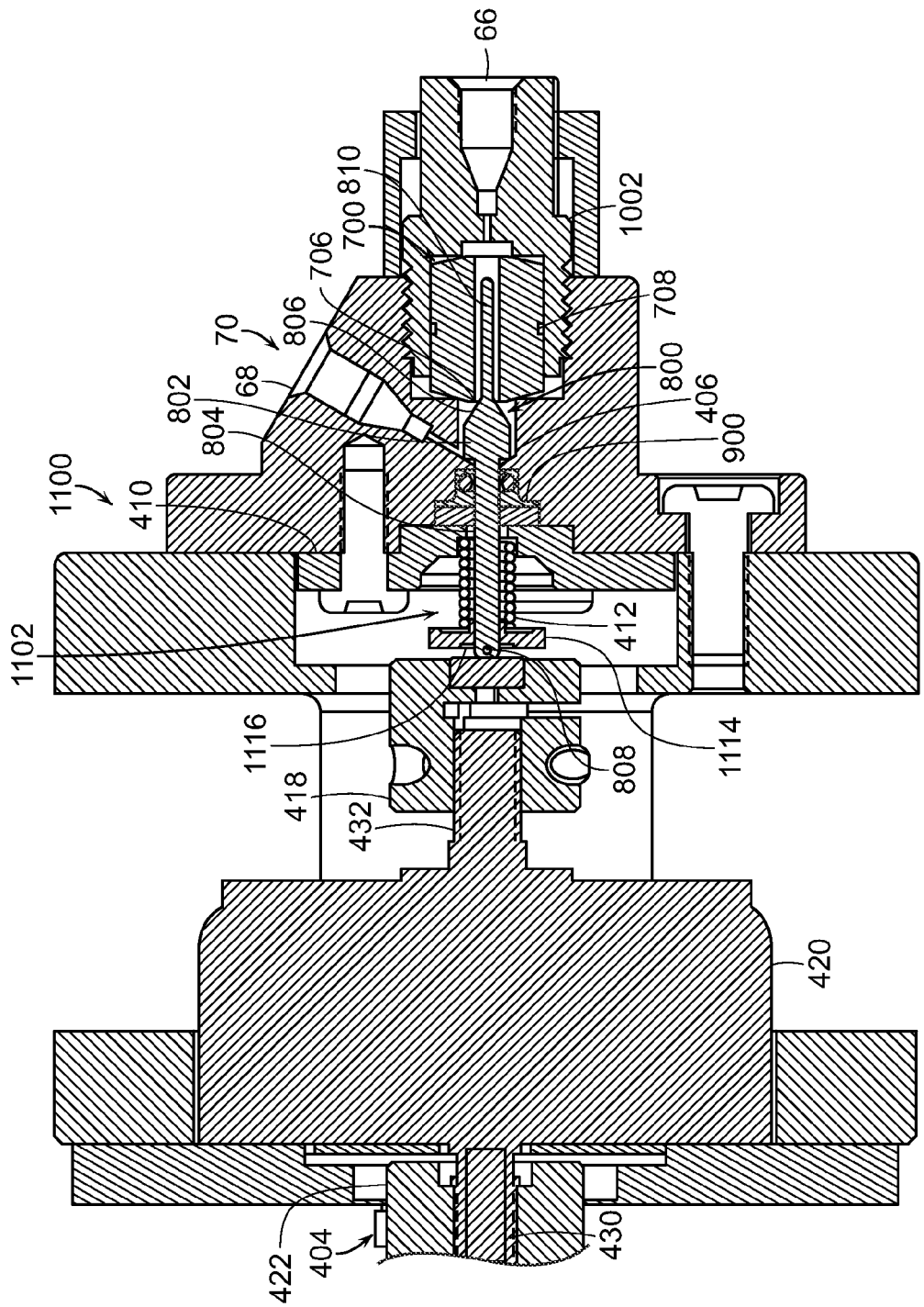
FIG. 30 is a detailed view of an exemplary embodiment of a push-in solenoid valve in an open position.

Turning now to FIG. 30, a detailed cross-sectional view of the exemplary push-in solenoid valve 1100 is provided with specific focus on the head section 70 in an open configuration. The seat 700 is securely disposed inside the seat retainer 1002. The seat retainer 1002 can be securely fastened inside the head section 70 by, e.g., matching threading on an outer surface of the seat retainer 1002 and an inner surface of the valve body 64. The solenoid valve 1100 is illustrated actuated into an open position, i.e., a flow path opening exists between the angular sealing surface 806 and the bore edge 706.

Figure 31:
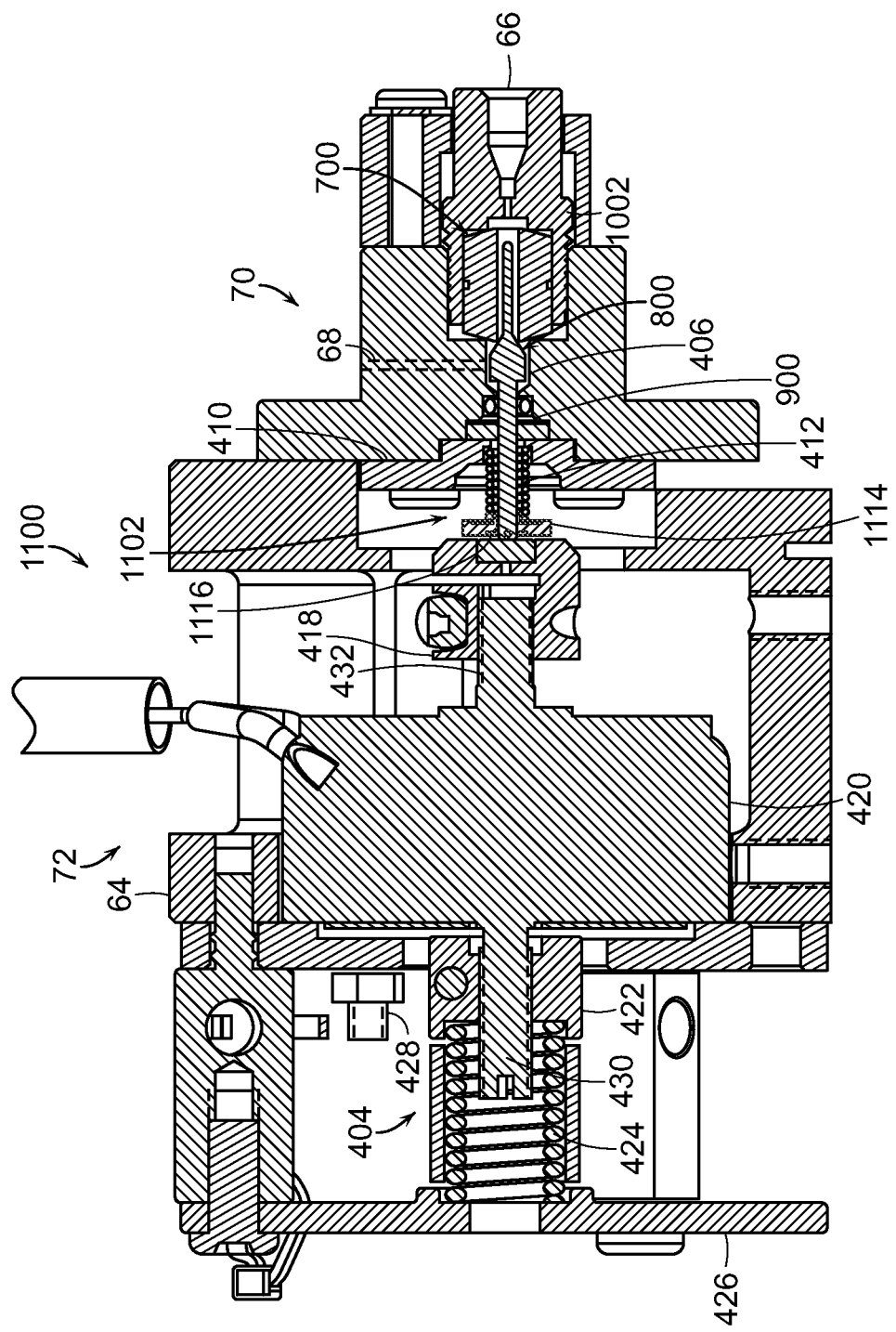
FIG. 31 is an exemplary embodiment of a push-in solenoid valve in a closed position according to the present disclosure.

With reference now to FIG. 31, an exemplary embodiment of a push-in solenoid valve 1100 is depicted in a closed position, i.e., a durable and/or tight seal is created between the angular sealing surface 806 of the needle 800 and the bore edge 706 of the seat 700. The components of the solenoid valve 1100 of FIG. 31 are substantially similar in configuration and/or function as those described with respect to the solenoid valve 1100 of FIGS. 27 and 30. However, the actuation of the solenoid valve 1100 of FIG. 31 into a closed position actuates the solenoid return spring mechanism 404 to permit the stem return spring mechanism 1102 to push the needle 800 into the seat 700 to stop flow through the bore 702. In particular, as the stem return spring mechanism 402 pushes the needle 800 into the seat 700, a durable and/or tight waterproof seal is created between the angular sealing surface 806 of the needle 800 and the bore edge 706 of the seat 700.

Figure 32:
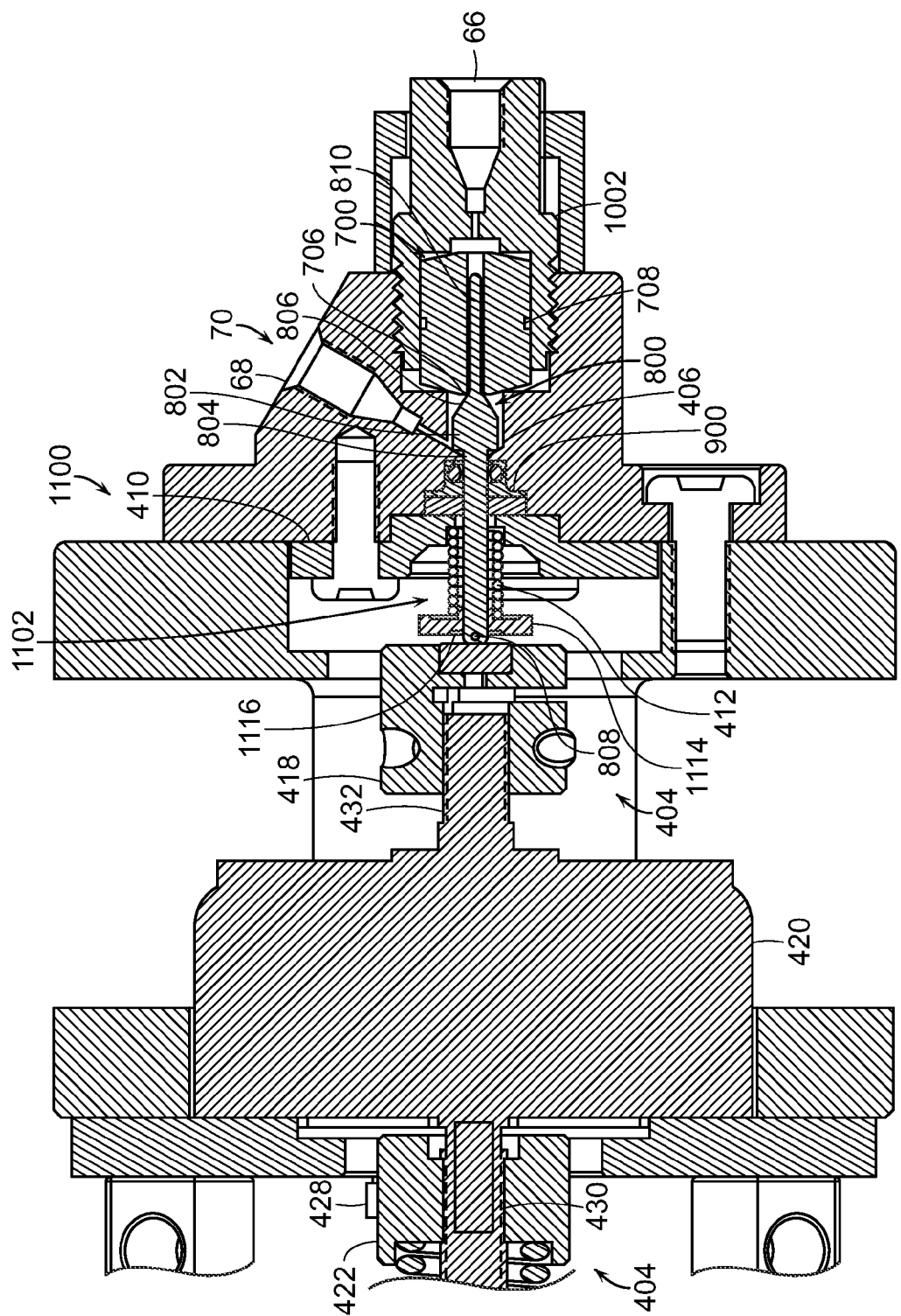
FIG. 32 is a detailed view of an exemplary embodiment of a push-in solenoid valve in a closed position.

FIG. 32 is a detailed cross-sectional view of the exemplary push-in solenoid valve 1100, with specific focus on the head section 70 in a closed configuration. As previously discussed, the closed configuration and/or position is created by actuating the solenoid return spring mechanism 404 to permit the stem return spring mechanism 1102 to push the needle 800 into the seat 700 to stop flow through the bore 702. The durable and/or tight waterproof seal between the angular sealing surface 806 and the bore edge 706 prevents leakage of the solvent 24 (e.g., mobile phase media 23) therebetween.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the technology.

The invention claimed is:

1. A modular solenoid valve kit, comprising:
   a valve body that includes a plurality of actuator section components and a plurality of head section components;
   wherein the plurality of actuator section components include a drive solenoid, a solenoid return spring, a stroke calibration collar, and an actuator-to-head calibration collar;
   wherein the plurality of head section components include a needle, a stem return spring, a seal, and a seat; and
   wherein the plurality of actuator section components and the plurality of head section components are adapted to be interchanged to create (i) a pull-through normally open valve, (ii) a pull-through normally closed valve, (iii) a push-in normally open valve, and (iv) a push-in normally closed valve.

2. The kit of claim 1, wherein interchanging the plurality of actuator section components and the plurality of head section components permits an alteration of at least a solenoid stroke, a solenoid return spring force, a pull-through needle and seat configuration, a push-in needle and seat configuration, an actuator to stem gap, a stem return spring force, a pressure assisted closure, and a pressure assisted opening.

3. The kit of claim 2, wherein the solenoid return spring force and the stem return spring force can be altered to accommodate a desired load in the valve body.

4. The kit of claim 1, wherein the stroke calibration collar and the actuator-to-head calibration collar are threaded.

5. The kit of claim 1, wherein the seat includes a bore extending therethrough.

6. The kit of claim 1, wherein the needle includes a needle stem and a needle head.

7. The kit of claim 2, wherein a push-in needle is implemented in a push-in needle and seat configuration.

8. The kit of claim 7, wherein the push-in needle is configured to be pushed into the seat to stop flow through a bore of the seat.

9. The kit of claim 2, wherein a pull-through needle is implemented in a pull-through needle and seat configuration.

10. The kit of claim 9, wherein the pull-through needle is configured to be pulled through the seat to stop flow through a bore of the seat.

11. The kit of claim 1, wherein the needle comprises an exterior coating.

12. The kit of claim 11, wherein the exterior coating is at least one of a gold coating, a platinum coating, a ceramic coating, and a polymer coating.

13. The kit of claim 6, wherein the needle includes a needle tip.

14. The kit of claim 6, wherein a needle head diameter is greater than a needle stem diameter.

15. The kit of claim 13, wherein a needle head diameter is greater than a needle tip diameter.

16. The kit of claim 14, wherein the needle comprises an angular sealing surface between the needle stem and the needle head for self-centering and aligning the needle during translation through the seat.

17. The kit of claim 15, wherein the needle comprises an angular sealing surface between the needle head and the needle tip for self-centering and aligning the needle during translation into the seat.

18. The kit of claim 16, wherein for a created pull-through normally open valve the solenoid return spring is configured to actuate to permit the stem return spring to pull the needle through the seat to stop flow through a bore of the seat.

19. The kit of claim 18, wherein the angular sealing surface is pulled against a bore edge of the seat to stop flow through the bore.

20. The kit of claim 19, wherein a plastic deformation of the bore edge occurs during pulling of the angular sealing surface against the bore edge.

21. The kit of claim 20, wherein the plastic deformation conforms a bore edge geometry to a complimentary angular sealing surface geometry.

22. The kit of claim 21, wherein the plastic deformation of the bore edge geometry ensures a fluid-tight seal against the angular sealing surface.

23. The kit of claim 22, comprising a pressure force to enhance the fluid-tight seal against the angular sealing surface.

24. The kit of claim 14, wherein a bore diameter is greater than the needle stem diameter.

25. The kit of claim 6, wherein the needle head comprises at least one head groove on a needle head face.

26. The kit of claim 6, wherein the needle stem comprises at least one stem groove.

27. The kit of claim 18, wherein pulling the needle through the seat to stop flow through the bore reduces an exposed volume of the valve body.

28. The kit of claim 16, wherein for a created pull-through normally closed valve the solenoid return spring is configured to actuate to push the needle through the seat to start flow through a bore of the seat.

29. The kit of claim 17, wherein for a created push-in normally open valve the solenoid return spring is configured to actuate to push the needle into the seat to stop flow through a bore of the seat.

30. The kit of claim 29, wherein the angular sealing surface is pushed against a bore edge of the seat to stop flow through the bore.

31. The kit of claim 30, wherein a plastic deformation of the bore edge occurs during pushing of the angular sealing surface against the bore edge.

32. The kit of claim 31, wherein the plastic deformation conforms a bore edge geometry to a complimentary angular sealing surface geometry.

33. The kit of claim 32, wherein the plastic deformation of the bore edge geometry ensures a fluid-tight seal against the angular sealing surface.

34. The kit of claim 33, comprising a pressure force to enhance the fluid-tight seal against the angular sealing surface.

35. The kit of claim 15, wherein a bore diameter is greater than the needle tip diameter.

36. The kit of claim 17, wherein for a created push-in normally closed valve the solenoid return spring is configured to actuate to permit the stem return spring to pull the needle out of the seat to start flow through a bore of the seat.

37. The kit of claim 1, wherein the seat is fabricated from at least one of a 30% carbon fiber filled PEEK material, a filled or unfilled grade PEEK material, and a filled or unfilled grade of polyimide plastic.

38. A method of fabricating a modular solenoid valve, comprising:
providing a valve body that includes a plurality of actuator section components and a plurality of head section components;
wherein the plurality of actuator section components include a drive solenoid, a solenoid return spring, a stroke calibration collar, and an actuator-to-head calibration collar;
wherein the plurality of head section components include a stem, a stem return spring, a seal, and a seat; and
interchanging the plurality of actuator section components and the plurality of head section components to create (i) a pull-through normally open valve, (ii) a pull-through normally closed valve, (iii) a push-in normally open valve, and (iv) a push-in normally closed valve.

* * * * *